United States Patent
Castro et al.

(10) Patent No.: US 8,541,581 B2
(45) Date of Patent: Sep. 24, 2013

(54) INHIBITORS OF FATTY ACID AMIDE HYDROLASE

(75) Inventors: Alfredo C. Castro, Winchester, MA (US); Catherine A. Evans, Somerville, MA (US); Louis Grenier, Newton, MA (US); Michael J. Grogan, Winchester, MA (US)

(73) Assignee: Infinity Pharmaceuticals, Inc., Cambridge, CA (US)

(*) Notice: Subject to any disclaimer, the term of this patent is extended or adjusted under 35 U.S.C. 154(b) by 0 days.

(21) Appl. No.: 13/263,324

(22) PCT Filed: Apr. 7, 2010

(86) PCT No.: PCT/US2010/030276
§ 371 (c)(1),
(2), (4) Date: Dec. 23, 2011

(87) PCT Pub. No.: WO2010/118159
PCT Pub. Date: Oct. 14, 2010

(65) Prior Publication Data
US 2012/0088738 A1 Apr. 12, 2012

Related U.S. Application Data

(60) Provisional application No. 61/167,464, filed on Apr. 7, 2009.

(51) Int. Cl.
C07F 5/02 (2006.01)

(52) U.S. Cl.
USPC .......................................................... 546/13

(58) Field of Classification Search
None
See application file for complete search history.

(56) References Cited

U.S. PATENT DOCUMENTS

| | | |
|---|---|---|
| 4,270,537 A | 6/1981 | Romaine |
| 4,596,556 A | 6/1986 | Morrow et al. |
| 4,790,824 A | 12/1988 | Morrow et al. |
| 4,853,150 A | 8/1989 | Bezborodov et al. |
| 4,886,499 A | 12/1989 | Cirelli et al. |
| 4,940,640 A | 7/1990 | Casey et al. |
| 4,941,880 A | 7/1990 | Burns |
| 5,015,235 A | 5/1991 | Crossman |
| 5,064,413 A | 11/1991 | McKinnon et al. |
| 5,089,499 A | 2/1992 | Barker et al. |
| 5,141,496 A | 8/1992 | Dalto et al. |
| 5,190,521 A | 3/1993 | Hubbard et al. |
| 5,198,149 A | 3/1993 | Reiffenrath et al. |
| 5,273,680 A | 12/1993 | Gray et al. |
| 5,312,335 A | 5/1994 | McKinnon et al. |
| 5,328,483 A | 7/1994 | Jacoby |
| 5,328,637 A | 7/1994 | Buchecker et al. |
| 5,334,144 A | 8/1994 | Alchas et al. |
| 5,339,163 A | 8/1994 | Homma et al. |
| 5,340,898 A | 8/1994 | Cavezzan et al. |
| 5,383,851 A | 1/1995 | McKinnon et al. |
| 5,417,662 A | 5/1995 | Hjertman et al. |
| 5,417,885 A | 5/1995 | Suzuki et al. |
| 5,466,220 A | 11/1995 | Brenneman |
| 5,480,381 A | 1/1996 | Weston |
| 5,503,627 A | 4/1996 | McKinnon et al. |
| 5,520,639 A | 5/1996 | Peterson et al. |
| 5,527,288 A | 6/1996 | Gross et al. |
| 5,541,061 A | 7/1996 | Fodor et al. |
| 5,543,075 A | 8/1996 | Parri et al. |
| 5,550,236 A | 8/1996 | Schlosser et al. |
| 5,569,189 A | 10/1996 | Parsons |
| 5,576,220 A | 11/1996 | Hudson et al. |
| 5,599,302 A | 2/1997 | Lilley et al. |
| 5,616,582 A | 4/1997 | Barker |
| 5,643,893 A | 7/1997 | Benson et al. |
| 5,649,912 A | 7/1997 | Peterson |

(Continued)

FOREIGN PATENT DOCUMENTS

| | | |
|---|---|---|
| DE | 4014488 A1 | 11/1991 |
| DE | 4220065 | 12/1993 |
| DE | 4445224 | 6/1996 |
| DE | 19710614 A1 | 9/1998 |
| DE | 19909761 | 10/1999 |
| DE | 19858594 A1 | 6/2000 |
| DE | 10009714 | 9/2001 |
| DE | 102005037925 | 2/2007 |
| DE | 102007009944 | 9/2007 |
| EP | 0440082 A2 | 8/1991 |

(Continued)

OTHER PUBLICATIONS

Polivka et al., Hydroboration of Unsaturated Amines. VI. Hydroboration of 1-methyl-3-piperideine and 1,3-dimethyl-3-piperideine, 35(8) Coll. Czechoslovak Chem. Commnc'ns, 2392-7 (1970) (CAS Abstract).*

(Continued)

*Primary Examiner* — Janet Andres
*Assistant Examiner* — Timothy R Rozof
(74) *Attorney, Agent, or Firm* — Jones Day

(57) ABSTRACT

Provided herein are compounds of formula (I): or pharmaceutically acceptable salts, solvates or prodrugs thereof or mixtures thereof, wherein $Z^1, Z^2, X^1, X^2, X^3, R^1, R^2, R^3, R^4$, m and n are defined herein. Also provided are pharmaceutically acceptable compositions that include a compound of formula I and a pharmaceutically acceptable excipient. Also provided are methods for treating an FAAH-mediated disorder comprising administering to a subject in need thereof a therapeutically effective amount of a compound or composition of the present invention.

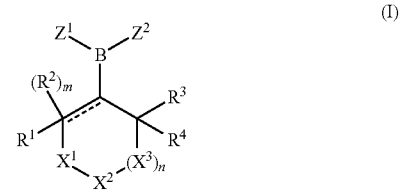

(I)

25 Claims, No Drawings

(56) References Cited

U.S. PATENT DOCUMENTS

| | | |
|---|---|---|
| 5,683,623 A | 11/1997 | Chan et al. |
| 5,693,688 A | 12/1997 | Priou |
| 5,704,911 A | 1/1998 | Parsons |
| 5,800,733 A | 9/1998 | Kelly |
| 5,847,149 A | 12/1998 | Fuss et al. |
| 5,849,958 A | 12/1998 | Barnes et al. |
| 5,892,131 A | 4/1999 | Barnes et al. |
| 5,893,397 A | 4/1999 | Peterson et al. |
| 5,993,412 A | 11/1999 | Deily et al. |
| 5,998,673 A | 12/1999 | Barnes et al. |
| 6,075,014 A | 6/2000 | Weston et al. |
| 6,096,784 A | 8/2000 | Lerner et al. |
| 6,174,458 B1 | 1/2001 | Koga et al. |
| 6,177,440 B1 | 1/2001 | Bach et al. |
| 6,218,445 B1 | 4/2001 | Priou et al. |
| 6,262,319 B1 | 7/2001 | Barnes et al. |
| 6,271,015 B1 | 8/2001 | Gilula et al. |
| 6,309,406 B1 | 10/2001 | Jones et al. |
| 6,326,156 B1 | 12/2001 | Civelli et al. |
| 6,344,474 B1 | 2/2002 | Maruani et al. |
| 6,423,378 B1 | 7/2002 | Cotting et al. |
| 6,600,066 B1 | 7/2003 | Schottek et al. |
| 6,617,125 B2 | 9/2003 | Adler, Jr. |
| 6,753,046 B2 | 6/2004 | Manabe et al. |
| 6,818,260 B2 | 11/2004 | Farrand et al. |
| 6,911,235 B2 | 6/2005 | Frances |
| 6,924,269 B2 | 8/2005 | Miljkovic et al. |
| 6,927,216 B2 | 8/2005 | Cherney et al. |
| 7,037,905 B2 | 5/2006 | Ebdrup et al. |
| 7,037,938 B2 | 5/2006 | Hattori et al. |
| 7,049,304 B2 | 5/2006 | Holmes-Farley et al. |
| 7,074,836 B1 | 7/2006 | Kawada et al. |
| 7,101,915 B1 | 9/2006 | Kawada et al. |
| 7,148,219 B2 | 12/2006 | Lou et al. |
| 7,183,447 B2 | 2/2007 | Pauluth et al. |
| 7,220,783 B2 | 5/2007 | Kawada et al. |
| 7,320,972 B2 | 1/2008 | Martinez et al. |
| 7,351,452 B2 | 4/2008 | Goodby et al. |
| 7,351,728 B2 | 4/2008 | Brooks et al. |
| 7,411,100 B2 | 8/2008 | Pauluth et al. |
| 7,425,281 B2 | 9/2008 | Wand et al. |
| 7,432,375 B2 | 10/2008 | Graczyk et al. |
| 7,521,455 B2 | 4/2009 | Nagase et al. |
| 7,553,496 B2 | 6/2009 | Ambati |
| 7,582,621 B2 | 9/2009 | Baker et al. |
| 7,626,020 B2 | 12/2009 | Butlin et al. |
| 7,645,776 B2 | 1/2010 | Ackermann et al. |
| 7,767,277 B2 | 8/2010 | Lietzau et al. |
| 7,776,922 B2 | 8/2010 | Bruggemeier et al. |
| 7,999,137 B2 | 8/2011 | Kunz et al. |
| 2002/0164769 A1 | 11/2002 | Curtis et al. |
| 2003/0096854 A1 | 5/2003 | Lin et al. |
| 2004/0115475 A1 | 6/2004 | Hashimoto |
| 2004/0204473 A1 | 10/2004 | Lin et al. |
| 2005/0090383 A1 | 4/2005 | Thiele et al. |
| 2006/0058527 A1 | 3/2006 | Kirsch et al. |
| 2006/0211698 A1 | 9/2006 | Boryanski et al. |
| 2006/0293502 A1 | 12/2006 | Dreyer et al. |
| 2007/0010559 A1 | 1/2007 | Christiansen et al. |
| 2007/0015003 A1 | 1/2007 | Hwang et al. |
| 2007/0082877 A1 | 4/2007 | Dunkel et al. |
| 2007/0125712 A1 | 6/2007 | Little et al. |
| 2008/0188371 A1 | 8/2008 | Fischer et al. |
| 2008/0242708 A1 | 10/2008 | Dunkel et al. |
| 2009/0005321 A1 | 1/2009 | Zimmer et al. |
| 2009/0099131 A1* | 4/2009 | Adams et al. .................. 514/64 |

FOREIGN PATENT DOCUMENTS

| | | |
|---|---|---|
| EP | 145441 B1 | 3/1992 |
| EP | 562897 A1 | 9/1993 |
| EP | 614958 A1 | 9/1994 |
| EP | 792883 B1 | 12/1997 |
| EP | 811593 A1 | 12/1997 |
| EP | 811596 A1 | 12/1997 |
| EP | 0987238 | 3/2000 |
| EP | 1160233 | 12/2001 |
| EP | 1236726 | 9/2002 |
| EP | 1388538 | 2/2004 |
| EP | 0952149 | 6/2004 |
| EP | 1444981 | 8/2004 |
| FR | 2727416 A1 | 5/1996 |
| FR | 2758329 | 1/1997 |
| GB | 2258232 | 2/1993 |
| GB | 2280181 | 1/1995 |
| GB | 2344817 A | 6/2000 |
| GB | 2410745 | 8/2005 |
| GB | 2424881 | 10/2006 |
| JP | 7145174 | 6/1995 |
| JP | 7165717 | 6/1995 |
| JP | 7206715 | 8/1995 |
| JP | 8092137 | 4/1996 |
| JP | 9278676 A | 10/1997 |
| JP | 10025261 | 1/1998 |
| JP | 10059882 | 3/1998 |
| JP | 2000001463 | 1/2000 |
| JP | 2000035596 A | 2/2000 |
| JP | 2000336045 A | 12/2000 |
| JP | 2002284768 A | 10/2002 |
| JP | 3555325 B2 | 8/2004 |
| JP | 2005162660 | 6/2005 |
| JP | 5331107 A | 12/2005 |
| JP | 2006290786 | 10/2006 |
| JP | 2007308483 | 11/2007 |
| JP | 8040953 A | 2/2008 |
| JP | 9030996 A | 2/2009 |
| PL | 167141 | 7/1995 |
| WO | 9219707 | 11/1992 |
| WO | 9415920 | 7/1994 |
| WO | 9512655 | 5/1995 |
| WO | 9535300 | 12/1995 |
| WO | 9620689 | 7/1996 |
| WO | 9706124 | 2/1997 |
| WO | 9713537 | 4/1997 |
| WO | 9733705 | 10/1997 |
| WO | 9824396 | 6/1998 |
| WO | 9828663 | 7/1998 |
| WO | 9831688 | 7/1998 |
| WO | 9835924 | 8/1998 |
| WO | 9934850 | 7/1999 |
| WO | 0004111 | 1/2000 |
| WO | 0020466 | 4/2000 |
| WO | 0042213 | 7/2000 |
| WO | 0121606 | 3/2001 |
| WO | 0214381 | 2/2002 |
| WO | 02057273 | 7/2002 |
| WO | 02059155 | 8/2002 |
| WO | 02085916 | 10/2002 |
| WO | 03045228 | 6/2003 |
| WO | 03059903 | 7/2003 |
| WO | 03064484 | 8/2003 |
| WO | 03105860 | 12/2003 |
| WO | 2004004169 A2 | 5/2004 |
| WO | 2004080989 | 9/2004 |
| WO | 2004081008 | 9/2004 |
| WO | 2005004799 | 1/2005 |
| WO | 2005013892 | 2/2005 |
| WO | 2005037227 | 4/2005 |
| WO | WO 2005/041904 | 5/2005 |
| WO | WO 2005/092863 | 10/2005 |
| WO | 2006007384 | 1/2006 |
| WO | 2006024389 | 3/2006 |
| WO | 2006050053 | 5/2006 |
| WO | 2006050054 | 5/2006 |
| WO | 2006050236 | 5/2006 |
| WO | 2006053250 | 5/2006 |
| WO | 2006089067 | 8/2006 |
| WO | 2006091799 | 8/2006 |
| WO | 2006099261 | 9/2006 |
| WO | 2006122186 | 11/2006 |
| WO | 2006124713 | 11/2006 |
| WO | 2006133559 | 12/2006 |
| WO | 2007028104 | 3/2007 |
| WO | 2007031512 | 3/2007 |
| WO | 2007064809 | 6/2007 |

| WO | 2005080403 | 7/2007 |
| WO | 2007076875 | 7/2007 |
| WO | 2007078340 | 7/2007 |
| WO | 2007088148 | 8/2007 |
| WO | 2007095638 | 8/2007 |
| WO | WO 2007/104783 | 9/2007 |
| WO | 2007118318 | 10/2007 |
| WO | 2007146965 | 12/2007 |
| WO | 2008002674 | 1/2008 |
| WO | 2008014497 | 1/2008 |
| WO | 2008019743 | 2/2008 |
| WO | 2008020920 | 2/2008 |
| WO | 2008039829 | 4/2008 |
| WO | 2008047229 | 4/2008 |
| WO | 2008063300 A2 | 5/2008 |
| WO | 2008090780 | 7/2008 |
| WO | 2008105286 | 9/2008 |
| WO | 2008107480 | 9/2008 |
| WO | 2009011904 A1 | 1/2009 |
| WO | 2009138176 | 11/2009 |
| WO | 2009136646 | 12/2009 |
| WO | 2009126691 | 2/2010 |

OTHER PUBLICATIONS

Richard B. Silverman, The Organic Chemistry of Drug Design and Drug Action, Chapter 2: Drug Discovery, Design, and Development, Academic Press, p. 5-51 (1992).*
Johnson et al., Benzothiphene Piperazine and Piperidine Urea Inhibitors of Fatty Acid Amide Hydrolase (FAAH), 19 Bioorg. & Med. Chem. Letts. 2865-2869 (2009).*
Belfaitah et al., "1,3-Dipolar cycloadditions of azomethine ylides to alkenylboronic esters. Access to substituted boron analogues of β-proline and 3-hydroxypyrrolidines," Tetrahedron Lett. 45(9): 1969-1972 (2004).
Brown et al., "Chiral Synthesis via Organoboranes. 6. Hydroboration. 74. Asymmetric Hydroboration of Representative Heterocyclic Olefins with Diisopinocamphcylborane. Synthesis of Heterocyclic Boronates and Heterocyclic Alcohols of Very High Enantiomeric Purity," J. Am. Chem. Soc. 108:2049-2054 (1986).
Dicko et al., "New Preparation of Aminoboronic Acids," Synthetic Communications 18(5):459-463 (1988).
Eastwood, "A versatile synthesis of 4-aryl tetrahydropyridines via palladium mediated Suzuki cross-coupling with cyclic vinyl boronates," Tetrahedron Lett. 41:3705-3708 (2000).
Deutsch, "Design of On-Target FAAH Inhibitors," Chem. Biol. 12(11):1157-1158 (2005).
Huang et al., "Identification of a new class of molecules, the arachidonyl amino acids, and characterization of one member that inhibits pain," J. Biol. Chem. 276(46):42639-42644 (2001).
Karbarz, et al., "Biochemical and Biological Properties of 4-(3-phenyl-[1,2,4]thiadiazol-5-yl)-piperazine-I-carboxylic acid phenylamide, a Mechanism-Based Inhibitor of Fatty Acid Amide Hydrolase," Anesthesia & Analgesia 108, 316-329 (2009).
Kathuria et al., "Modulation of anxiety through blockade of anandamide hydrolysis," Nat. Med. 9(1):76-81 (2003).
McPartland et al., "A shifted repertoire of endocannabinoid genes in the zebrafish (Danio rerio)," Mol. Genet. Genomics 277:555-570 (2007).
Mendelson and Basile, "The Hypnotic Actions of the Fatty Acid Amide, Oleamide," Neuropsychopharmacology 25(5 Suppl):S36-S39 (2001).
Saghetelian et al., "A FAAH-regulated class of N-acyl taurines that activates TRP ion channels," Biochemistry 45(30):9007-9015 (2006).
Walker et al., "Pain modulation by release of the endogenous cannabinoid anandamide," Proc. Natl. Acad. Sci. U. S. A. 96(21):12198-203 (1999).
Zhang et al., "Studies on antitumor drugs. II. Synthesis of diarylborinic .alpha.-amino acid anhydrides and diarylborinic aminoethyl esters," XP002663674, Retrieved from STN Database Accession No. 1983:17023.
Adamo et al., "Mechanism of the Palladium-Catalyzed Homocoupling of Arylboronic Acids: Key Involvement of a Palladium Peroxo Complex," JACS 128:6829-6836 (2006).

Asano et al., "Design, Synthesis, and Biological Evaluation of Amnioboronic Acids as Growth-Factor Receptor Inhibitors of EGFR and VEGFR-1 Tyrosine Kinases," ChemBioChem. 5:483-490 (2004).
Bellina et al., "Palladium Catalysts for the Suzuki Cross-Coupling Reaction: An Overview of Recent Advances," Syn. 2419-2440 (2004).
Berge et al., "Pharmaceutical Salts," J Pharm Sci. 66(1):1-19 (1977).
Bickerdike et al., "The Influence of 5-Hydroxytryptamine Re-uptake Blockade on CCK Receptor Antagonist Effects in the Rat Elevated Zero-Maze," Eur. J. Pharm. 271:403-411 (1994).
Bracey et al., "Structural Adaptations in Membrane Enzyme That Terminates Endocannabinoid Signaling," Science 298:1793-1796 (2002).
Buzzoni et al., "Aza-boronic Acids as Non- β-Lactam Inhibitors of AmpC- β-Lactamase," Bioorganic & Medicinal Chemistry Letters 14:3979-3983 (2004).
Carter et al., "The Inhibition of Rat Liver Chromatin Potease by Congeners of the Phenyboronic Acids," Biochim. Biophys. Acta (484)1:103-108 (1977).
CAS File Registry, Registry for [4-[2-(2,6-difluoro-4-propylphenyl)ethyl]-2,6-difluorophenyl]-boronic acid, published Mar. 3, 2003 in Japanese Patent Application No. JP10059882.
CAS File Registry, Registry No. 874288-40-1, published Feb. 15, 2006.
CAS File Registry, Registry No. 874289-19-7, published Feb. 15, 2006.
CAS File Registry, Registry No. 874290-59-2, published Feb. 15, 2006.
Caujolle et al., "Arylboronic Acid Metabolism in The Rat," Sciences Naturelles 270(11):1529-1531 (1970). (English translation of Abstract provided).
Caujolle et al., "Etude comparee du pouvoir renforcateur des organoboriques a l'egard des hypnotiques// potentiation of hypnotics by organoboron derivatives," Agressologie 10(1):51-54 (1969). (English translation of Summary provided).
Caujolle et al., "The effect of organoboron derivatives on cardiovascular and ventilatory manifestations of electroshock," Agressologie: Revue Internationale De Physio-Biologie et de Pharmacologie Appliquees aux Effets de I'Agression, 8(5):425-432 (1967).
Cravatt et al., "Functional disassociation of the central and peripheral fatty acid amide signaling systems," Proc. Natl. Acad. Sci. U.S.A. 101(29):10821-10826 (2004).
Cravatt et al., "Supersensitivity to Anandamide and Enhanced Endogenous Cannabinoid Signaling in Mice Lacking Fatty Acid Amide Hydrolase," Proc. Natl. Acad. Sci. U.S.A. 98:9371-9376 (2001).
Dong et al., "The synthesis and transition temperatures of some fluorinated terphenyls with chiral and alkenyl terminal chains," Ferroelectrics (180):245-257 (1996).
Drake et al., "Characterizing high-affinity antigen/antibody complexes by kinetic- and equilibrium-based methods," Anal. Biochem. 328(1):35-43 (2004).
Ebdrup et al., "Structure-activity relationship for aryl and heteroaryl boronic acid inhibitors of hormone-sensitive lipase," Bioorg. Med. Chem. 13(6):2305-2312 (2005).
Gavezzotti, "Are Crystal Structures Predictable?" Acc. Chem. Res. 27:309-314 (1994). (From 892 11/870,130).
Giang and Cravatt, "Molecular characterization of human and mouse fatty acid amide hydrolases," Proc. Natl. Acad. Sci. U.S.A. 94(6):2238-2242 (1997).
Glendinning et al., "The synthesis and mesomorphic properties of 2,2',3-tri- and 2,2',3,3'-tetra-fluoro-1,1':4',1"-terphenyls for high dielectric biaxiality ferroelectric liquid crystal mixtures," J. Chem. Soc. Perkin Trans. 2 (3):481-492 (1999).
Glendinning et al., "The synthesis and mesomorphic properties of 4,4"-dialkyl-2,2',3- and 2,2',3'-trifluoro-1,1':4',1"-terphenyls for high dielectric biaxiality ferroelectric liquid crystal mixtures," J. Chem. Soc. Perkin Trans. 2 27-34 (2000).
Gray et al., "The synthesis and transition-temperatures of some 4,4"-dialkyl-1,1'-4',1"-terphenyl and 4,4"-alkoxyalkyl-1,1'-4',1"-terphenyl with 2,3-difluoro or 2',3'-difluoro substituents and of their biphenyl analogs," J. Chem. Soc.-Perkin Trans. 2 2041-2053 (1989).

Helble, Joseph. "Determination of Boronic Acids Derivatized with Azomethine and HPLC Separation with Visible Wavelength Detection." American Association of Pharmaceutical Scientists National Convention, Los Angeles, Nov. 9, 2009.

Helble, Joseph. "Determination of Boronic Acids Derivatized with Azomethine and HPLC Separation with Visible Wavelength Detection." Mar. 6, 2009. Pittcon Analytical Chemistry Conference, Chicago, IL, Mar. 10, 2009.

Hillard et al., "Characterization of the kinetics and distribution of N-arachidonylethanolamine (anandamide) hydrolysis by rat brain," Biochim. Biophys. Acta. 1257(3):249-256 (1995).

Hird et al., "Cyclohexenyl triflates and arylboronic acids in palladium-catalysed cross-couplings. Synthesis and transition temperatures of some fluoro-substituted biphenylylcyclohexenes," J. Mater. Chem. (5):2239-2245 (1995).

Hird et al., "The relationship between molecular structure and mesomorphic properties of 2,2'- and 3,2'-difluoroterphenyls synthesized by palladium-catalysed cross-couplings," Liquid Crystals 18(1):1-11 (1995).

Innocenti et al., "Carbonic Anhydrase Inhibitors. Inhibition of Fungal β-Carbonic Anhydrases from Candida Albicans and *Cryptococcus neoformans* with Boronic Acids," Bioorganic & Medicinal Chemistry Letters 1-4 (2009).

Insel et al., "Rat Pup Ultrasonic Calls: Possible Mediation by the Benzodiazepine Receptor Complex," Pharmacol. Biochem. Behav. 24:1263-1267 (1986).

Jauhiainen et al., "Aromatic Boronic Acids as Probes of the Catalytic Site of Human Plasma Lecithin-Cholesterol Acyltransferase," Biochem. Biophys. Acta. 918:175-188 (1987).

Jiang et al., "Use of in Situ Isopropoxide Protection in the Metal-Halogen Exchange of Arylboronates," J. Org. Chem. 72:6618-6620 (2007).

Jun et al., "Determination of Boron with Chromotropic Acid by High-performance Liquid Chromatography," Analyst 113:1631-1634 (1988).

Kedia et al., "Reaction Progress Analysis: Powerful Tool for Understanding Suzuki-Miyura Reaction and Control of Polychlorobiphenyl Impurity," Org. Proc. Res. Dev. 13:420-428 (2009).

Koehler et al., "2-Phenylethaneboronic Acid, a Possible Transition-State Analog for Chymotrypsin," Biochemistry 10:2477 (1971).

Kong et al., "Structure-Based Discovery of a Boronic Acid Biosostere of Combretastatin A-4," Chem. Biol. 12 (9):1007-1014 (2005).

Labar et al., "Fatty Acid Amide Hydrolase: From Characterization to Therapeutics," Chem. Biodivers. 4(8):1882-1902 (2007).

Lambert and Fowler, "The endocannabinoid system: Drug targets, lead compounds, and potential therapeutic applications," J. Med. Chem. 48(16):5059-5087 (2005).

Li et al., "An Improved Protocol for the Preparation of 3-Pyridyl- and Some Arylboronic Acids," J. Org. Chem. 67:5394-5397 (2002).

Lienhard et al., "2 Phenylethaneboronic Acid, A Possible Transition-State Analog for Chymotrypsin," Biochemistry 10(13):2477-2483 (1971).

Lynch et al., "Effects of Neuropeptide Y on Ingestion of Flavored Solutions in Nondeprived Rats," Physiol. Behav. 54:877-880 (1993).

Martin et al., "Inhibition of the RTEM-1 β-Lactamase by Boronic Acids," Bioorg. Med. Chem. Lett. 4:1229-1234 (1994).

Maurelli et al, "Two novel classes of neuroactive fatty acid amides are substrates for mouse neuroblastoma 'anandamide amidohydrolase'," FEBS Lett. 377(1):82-86 (1995).

McKinney et al., "Structure and Function of Fatty Acid Amide Hydrolase," Ann. Rev. Biochem. 74:411-432 (2005).

Miczek, et al., "Aggression, Anxiety and Vocalizations in Animals: GABAa and 5-HT Anxiolytics," Psychopharmacology 121:38-56 (1995).

Miller et al., "Suppression of a Palladium-Mediated Homocoupling in a Suzuki Cross-Coupling Reaction. Development of an Impurity Control Strategy Supporting Synthesis of LY451395," Org. Proc. Res. Dev. 11:359-364 (2007).

Miller et al., "The Hypolipidemic and Anti-Inflammatory Activity of Boronated Aromatic Amino Acids in CF(1) Male Mice," Met. Based Drugs 6(6):337-344 (1999).

Minkkila et al., "Discovery of Boronic Acids as Novel and Potent Inhibitors of Fatty Acid Amide Hydrolase," J. Med. Chem. 51:7057-7060 (2008).

Miyaura et al., "Palladium-Catalyzed Cross—Coupling Reactions of Organoboron Compounds," Chem. Rev. 95:2457-2483 (1995).

Morandi et al., "Nanomolar Inhibitors of AmpC β-Lactamase," J. Am. Chem. Soc. 125:685-695 (2003).

Nakamura et al., "Synthesis and Biological Evaluation of Boronic Acid Containing cis-Stilbenes as Apoptotic Tubulin Polymerization Inhibitors," ChemMedChem 1:729-740 (2006).

Negishi et al., "Formation of Carbon-Carbon and Carbon-Heteroatom Bonds via Organoboranes and Organoborates," Organic Reactions 33:1-78 (1985).

Pacher et al., "The endocannabinoid system as an emerging target of pharmacotherapy," Pharmacol. Rev. 58 (3):389-462 (2006).

Patricelli et al., "Comparative characterization of a wild type and transmembrane domain-deleted fatty acid amide hydrolase: identification of the transmembrane domain as a site for oligomerization," Biochemistry 37(43):15177-15187 (1998).

Philipp et al., "Inhibition of Serine Proteases by Arylboronic Acids," Proc. Natl. Acad. Sci. U.S.A. 68(2):478-480 (1971).

Pillarisetti et al., "Pain and beyond: fatty acide amides and fatty acide amide hydrolase inhibitors in cardiovascular and metabolic diseases," Drug Discov. 1-14 (2009).

Piomelli et al., "Pharmacological Profile of the Selective FAAH Inhibitor KDS-4103 (URB597)," CNS Drug Rev. 12 (1):21-38 (2006).

Porsolt et al., "Depression: A New Animal Model Sensitive to Antidepressant Treatments," Nature 266:730-732 (1977).

Prasad et al., "Synthesis of Novel 3-Aryl-N-Methyl-1,2,5,6-Tetrahydropyridine Derivatives by Suzuki coupling: As Acetyl Cholinesterase Inhibitors," Open Med. Chem. J. 1:4-10 (2007).

Quistad et al., "Fatty Acid Amide Hydrolase Inhibition by Neurotoxic Organophosphous Pesticides," Toxicol. Appl. Pharmacol. 173(1):48-55 (2001).

Ramarao et al., "A Fluorescence-Based Assay for Fatty Acid Amide Hydrolase Compatible with High-Throughput Screening," Anal. Biochem. 343:143-151 (2005).

RN 874288-40-1 (Entered STN: Feb. 15, 2006).
RN 874289-19-7 (Entered STN: Feb. 15, 2006).
RN 874290-59-2 (Entered STN: Feb. 15, 2006).

Rock et al., "An Anti-Fungal Agent Inhibits an Aminoacyl-tRNA Synthetase by Trapping tRNA in the Editing Site," Science 316:1759-1761(2007).

Santucci et al., "Some Bromine-containing and Sulfur-containing Aromatic Boronic Acids," JACS 80:193-196 (1958).

Schlosburg et al., "Targeting Fatty Acide Amide Hydrolase (FAAH) to Treat Pain and Inflammation," The AAOS J. 11(1):39-44 (2009).

Seufer-Wasserthal et al., "Probing the Specificity of the S1 BindingSite of Subtilisin Carlsberg with Boronic Acids," Bioorg. Med. Chem. Lett. 2(1):35-48 (1994).

Shepherd et al., "Behavioural and Pharmacological Characterisation of the Elevated "Zero-Maze" as an Animal Model of Anxiety," Psychopharmacology 116:56-64 (1994).

Simpelkamp et al., "Boronic Acid Inhibitors as Probes of the Factors Involved in Binding at the Active Sites of Subtilisin Carlsberg and α-Chymotrypsin," Bioorg. Med. Chem. Lett. 2(11):1391-1394 (1994).

Smoum et al., "A study of the effect on nucleophilic hydrolytic activity of pancreatic elastase, trypsin, chymotrypsin, and leucine aminopeptidase by boronic acids in the presence of arabinogalactan: a subsequent study on the hydrolytic activity of chymotrypsin by boronic acids in the presence of mono-, di-, and trisaccharides," Bioorg. Chem. 31 (6):464-474 (2003).

Smoum et al., "Noncovalent Inhibition of the Serine Proteases, α-chymotrypsin and Trypsin by Trifluoro(organo) borates," Org. Biomol. Chem. 3(5):941-944 (2005).

Snyder et al., "Aryl Boronic Acids. II. Aryl Boronic Anhydrides and Their Amine Complexes," JACS 80:3611 (1958).

Soloway, A.H., "Correlation of drug penetration of brain and chemical structure," Science 128(3338):1572-1574 (1958).

Steru et al., "The Tail Suspension Test: A New Method for Screening Antidepressants in Mice," Psychopharmacology 85:367-370 (1985).

Suzuki et al., "Design, Synthesis, and Biological Activity of Boronic Acid-Based Histone Deacetylase Inhibitors," J. Med. Chem. 52(9): 2909-2922 (2009).

Tanaka et al., "Suppression of arthritis by the inhibitors of dipeptidyl peptidase IV," Int. J. Immunopharmacol. (19)1:15-24 (1997).

Tondi et al., "Structure-based design and in-parallel synthesis of inhibitors of AmpC β-lactamase," Chem. Biol. 8(6):593-610 (2001).

Uehara et al., "Determination of Trace Amounts of Boron in Steel by Reversed-Phase High-Performance Liquid Chromatography with Azomethine-H as a Precolumn Derivatization Agent," Anal. Sci. 17:1421-1424 (2001).

Vandervoorde, "Overview of the Chemical Families of Fatty Acid Amide Hydrolase and Monoacylglycerol Lipase Inhibitors," Curr. Top. Med. Chem. 8(3):247-267 (2008).

Vashchenko et al., "Palladium-catalyzed Suzuki Cross-coupling Reactions in a Microemulsion," Tetrahedron Lett. 49(9):1445-1449 (2008).

Vippagunta et al., "Crystalline Solids," Adv. Drug Deliv. Rev. 48(1):3-26 (2001).

Wang et al., "High-Throughput Screening for the Discovery of Inhibitors of Fatty Acid Amide Hydrolase Using a Microsome-Based Fluorescent Assay," J. Biomol. Screen. 11:519-527(2006).

Wang et al., "Preparation of Unsymmetrical Biaryls by Pd(II)-Catalyzed Cross-Coupling of Aryl Iodides," Org. Lett. 11:1079-1082 (2009).

Wei et al., "A second fatty acid amide hydrolase with variable distribution among placental mammals," J. Biol. Chem. 281(48):36569-36578 (2006).

Wermuth, C.G. (ed.), "Chapter 13: Molecular Variations Based on Isosteric Replacements", The Practice of Medicinal Chemistry, pp. 204-237, Academic Press Ltd., Copyright (1996).

Weston et al., "Structure-Based Enhancement of Boronic Acid-Based Inhibitors of AmpC β-Lactamase," J. Med. Chem. 41:4577-4586 (1998).

Wilen et al., "Strategies in Optical Resolution," Tetrahedron 33:2725-2736 (1977).

Willner, "Validity, Reliability and Utility of the Chronic Mild Stress Model of Depression: a 10-year Review and Evaluation," Psychopharmacology 134:319-329 (1997).

Winslow et al., "Infant Rat Separation is a Sensitive Test for Novel Anxiolyitics," Prog. Neuro-Psychopharmacol. & Biol. Psychiat. 15:745-757 (1991).

Winum et al., "Carbonic anhydrase inhibitors. Synthesis and inhibition of cytosolic/tumor-associated carbonic anhydrase isozymes I, II, and IX with boron-containing sulfonamides, sulfamides, and sulfamates: toward agents for boron neutron capture therapy of hypoxic tumors," Bioorg. Med. Chem. Lett. 15(13):3302-3306 (2005).

Yang et al., "Boronic Acid Compounds as Potential Pharmaceutical Agents," Med. Res. Rev. 23(3): 346-368 (2003).

Zhong et al., "Suzuki coupling of aryl organics on diamond," Chem. Mater. 20(9):3137-3144 (2008).

\* cited by examiner

INHIBITORS OF FATTY ACID AMIDE HYDROLASE

CROSS REFERENCE TO RELATED APPLICATIONS

This application is the national phase entry pursuant to 35 U.S.C. §371 of International Application No. PCT/US2010/030276, which has the international filing date of Apr. 7, 2010, and which claims priority to U.S. Provisional Application Ser. No. 61/167,464, filed Apr. 7, 2009, all of which are incorporated herein by reference in their entireties.

BACKGROUND

Fatty acid amide hydrolase (FAAH), also referred to as oleamide hydrolase and anandamide amidohydrolase, is an integral membrane protein that degrades fatty acid primary amides and ethanolamides, including oleamide and anandamide. FAAH degrades neuromodulating fatty acid amides at their sites of action and is intimately involved in their regulation.

FAAH has been demonstrated to be involved in a number of biological processes and its inhibition has been shown to be effective in treating a variety of conditions. For example, inhibiting FAAH has been shown to be useful in treating chronic pain, acute pain, neuropathic pain, anxiety, depression, feeding behaviors, movement disorders, glaucoma, neuroprotection and cardiovascular disease.

SUMMARY

Compounds described herein, and pharmaceutically acceptable compositions thereof, are effective inhibitors of fatty acid amide hydrolase (FAAH).

In one aspect, provided herein are compounds of formula I:

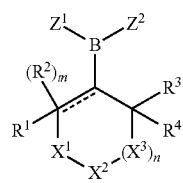

I or pharmaceutically acceptable salts, solvates or prodrugs thereof, or mixtures thereof,
wherein:
----- is selected from a single bond and a double bond;
m is 1 when ----- is a single bond;
m is 0 when ----- is a double bond;
$X^1$ is selected from $NR^5$ and $CR^6R^7$;
$X^2$ is selected from $NR^8$ and $CR^9R^{10}$;
$X^3$ is selected from $NR^{11}$ and $CR^{12}R^{13}$;
n is 0 or 1;
provided that at least one of $X^1$, $X^2$ and $X^3$ is selected from $NR^5$, $NR^8$ or $NR^{11}$;
$Z^1$ is selected from $-OR^{14}$ and $C_{1-6}$ alkyl;
$Z^2$ is selected from $-OR^{15}$ and $C_{1-6}$ alkyl;
or alternatively, $Z^1$ and $Z^2$, together with the boron atom to which they are bound, form a 5- to 8-membered ring having at least one O atom directly attached to the boron atom, wherein the ring is comprised of carbon atoms and optionally one or more additional heteroatoms independently selected from the group consisting of N, S, and O, and wherein the ring is with 1-4 substituents selected from halogen, $C_{1-6}$ alkyl, $C_{7-12}$ aralkyl, and oxo, and wherein the ring is optionally fused to an phenyl ring;

$R^1$, $R^2$, $R^3$, $R^4$, $R^6$, $R^7$, $R^9$, $R^{10}$, $R^{12}$ and $R^{13}$ each independently is selected from H, halogen, $C_{1-6}$ alkyl, $C_{2-6}$ alkenyl, $C_{2-6}$ alkynyl, $C_{1-6}$ perhaloalkyl, $-CN$, $-OR^{16}$, $NR^{17}R^{18}$, $-C(O)R^{19}$, $C_{3-10}$ carbocyclyl, $C_{6-10}$ aryl, $C_{7-12}$ aralkyl, 3-10 membered cycloheteroalkyl, and 5-10 membered heteroaryl;
$R^5$, $R^8$ and $R^{11}$ each independently is selected from H, $C_{1-6}$ alkyl, $C_{2-6}$ alkenyl, $C_{2-6}$ alkynyl, $-C(O)R^{20}$, $-C(O)OR^{21}$, $-C(O)NR^{22}R^{23}$, $S(O)_2R^{24}$, $C_{3-10}$ carbocyclyl, $C_{6-10}$ aryl, 3-10 membered cycloheteroalkyl, 5-10 membered heteroaryl, and $-(CH_2)_p-R^{25}$;
$R^{14}$ and $R^{15}$, at each occurrence, each independently is selected from H, $C_{1-6}$ alkyl, $C_{2-6}$ alkenyl, and $C_{2-6}$ alkynyl;
$R^{16}$, at each occurrence, each independently is selected from H, $C_{1-6}$ alkyl, $C_{2-6}$ alkenyl, $C_{2-6}$ alkynyl, $C_{3-10}$ carbocyclyl, $C_{6-10}$ aryl, $C_{7-12}$ aralkyl, 3-10 membered cycloheteroalkyl, and 5-10 membered heteroaryl;
$R^{17}$ and $R^{18}$, at each occurrence, each independently is selected from H, $C_{1-6}$ alkyl, $C_{2-6}$ alkenyl, $C_{2-6}$ alkynyl, $-C(O)R^{26}$, $-C(O)OR^{27}$, $C_{3-10}$ carbocyclyl, $C_{6-10}$ aryl, $C_{7-12}$ aralkyl, 3-10 membered cycloheteroalkyl, and 5-10 membered heteroaryl;
$R^{19}$, at each occurrence, each independently is selected from $C_{1-6}$ alkyl, $C_{2-6}$ alkenyl, $C_{2-6}$ alkynyl, $C_{3-10}$ carbocyclyl, $C_{6-10}$ aryl, $C_{7-12}$ aralkyl, 3-10 membered cycloheteroalkyl, and 5-10 membered heteroaryl;
$R^{20}$ and $R^{21}$ each independently is selected from $C_{1-6}$ alkyl, $C_{2-6}$ alkenyl, $C_{2-6}$ alkynyl, $C_{3-10}$ carbocyclyl, $C_{6-10}$ aryl, 3-10 membered cycloheteroalkyl, 5-10 membered heteroaryl, and $-(CH_2)_q-R^{28}$;
$R^{22}$ and $R^{23}$ each independently is selected from H, $C_{1-6}$ alkyl, $C_{2-6}$ alkenyl, $C_{2-6}$ alkynyl, $C_{3-10}$ carbocyclyl, $C_{6-10}$ aryl, 3-10 membered cycloheteroalkyl, 5-10 membered heteroaryl, and $-(CH_2)_r-R^{29}$;
$R^{24}$ is selected from $C_{1-6}$ alkyl, $C_{2-6}$ alkenyl, $C_{2-6}$ alkynyl, $C_{3-10}$ carbocyclyl, $C_{6-10}$ aryl, 3-10 membered cycloheteroalkyl, 5-10 membered heteroaryl, and $-(CH_2)_t-R^{30}$;
$R^{25}$ is selected from $C_{3-10}$ carbocyclyl, $C_{6-10}$ aryl, 3-10 membered cycloheteroalkyl, and 5-10 membered heteroaryl;
$R^{26}$ and $R^{27}$ each independently is selected from $C_{1-6}$ alkyl, $C_{2-6}$ alkenyl, $C_{2-6}$ alkynyl, $C_{3-10}$ carbocyclyl, $C_{6-10}$ aryl, $C_{7-12}$ aralkyl, 3-10 membered cycloheteroalkyl, and 5-10 membered heteroaryl;
$R^{28}$, $R^{29}$, and $R^{30}$, at each occurrence, each independently is selected from $-OR^{31}$, $-NR^{32}R^{33}$, $C_{3-10}$ carbocyclyl, $C_{6-10}$ aryl, 3-10 membered cycloheteroalkyl, and 5-10 membered heteroaryl;
$R^{31}$, $R^{32}$ and $R^{33}$, at each occurrence, each independently is selected from H, $C_{1-6}$ alkyl, $C_{2-6}$ alkenyl, $C_{2-6}$ alkynyl, $C_{3-10}$ carbocyclyl, $C_{6-10}$ aryl, $C_{7-12}$ aralkyl, 3-10 membered cycloheteroalkyl, and 5-10 membered heteroaryl; and
p, q, r, and t, at each occurrence, each independently is selected from 1, 2, 3, 4, 5 and 6.

In certain embodiments, the compound is of the formula III:

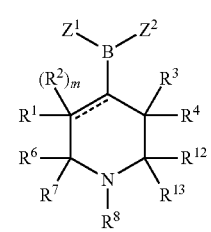

III or a pharmaceutically acceptable salt, solvate or prodrug thereof, or mixture thereof.

In certain embodiments, the compound is of the formulae IIIa or IIIb:

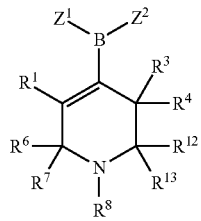
IIIa

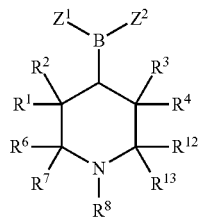
IIIb or a pharmaceutically acceptable salt, solvate or prodrug thereof, or mixture thereof.

In certain embodiments, the compound is of the formula VIII:

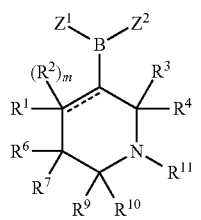
VIII or a pharmaceutically acceptable salt, solvate or prodrug thereof, or mixture thereof.

In certain embodiments, the compound is of the formulae VIIIa or VIIIb:

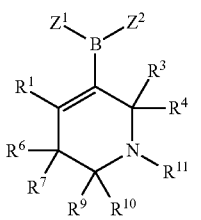
VIIIa

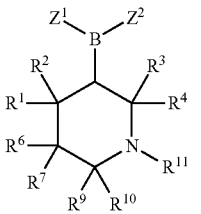
VIIIb or a pharmaceutically acceptable salt, solvate or prodrug thereof, or mixture thereof.

In certain embodiments, the compound is of the formula VI:

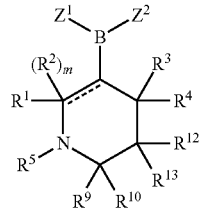
VI or a pharmaceutically acceptable salt, solvate or prodrug thereof, or mixture thereof.

In certain embodiments, the compound is of the formulae VIa or VIb:

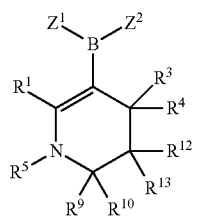
VIa

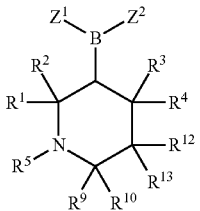
VIb or a pharmaceutically acceptable salt, solvate or prodrug thereof, or mixture thereof.

In certain embodiments, the compound of the formula IV:

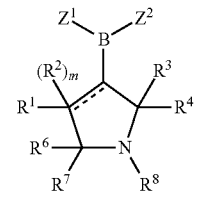
IV or a pharmaceutically acceptable salt, solvate or prodrug thereof, or mixture thereof.

In certain embodiments, the compound is of the formulae IVa or IVb:

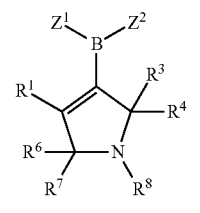
IVa

-continued

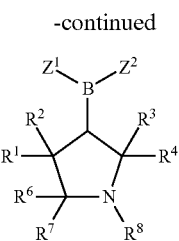
IVb or a pharmaceutically acceptable salt, solvate or prodrug thereof, or mixture thereof.

In certain embodiments, the compound is of the formula VII:

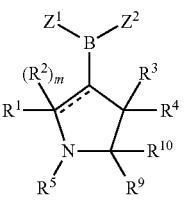
VII or a pharmaceutically acceptable salt, solvate or prodrug thereof, or mixture thereof.

In certain embodiments, the compound is of the formulae VIIa or VIIb:

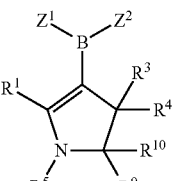
VIIa

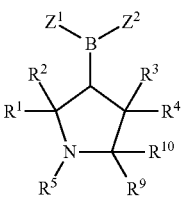
VIIb or a pharmaceutically acceptable salt, solvate or prodrug thereof, or mixture thereof.

In certain embodiments, ----- is a double bond and m is 0.
In certain embodiments, ----- is a single bond and m is 1.
In certain embodiments, $R^1$ is H.
In certain embodiments, $R^2$ is H.
In certain embodiments, $R^3$ is H and $R^4$ is H.
In certain embodiments, $Z^1$ is —$OR^{14}$ and $Z^2$ is —$OR^{15}$. In certain embodiments, $R^{14}$ is H and $R^{15}$ is H (i.e., wherein $Z^1$ and $Z^2$ are both —OH).
In certain embodiments, $X^1$ is $CR^6R^7$. In certain embodiments, $R^6$ is H and $R^7$ is H.
In certain embodiments, $X^2$ is $NR^8$. In certain embodiments, $R^8$ is selected from $C_{1-6}$ alkyl, —$C(O)R^{20}$, —$C(O)OR^{21}$, —$C(O)NR^{22}R^{23}$, $S(O)_2R^{24}$, and —$(CH_2)_p$—$R^{25}$.
In certain embodiments, $R^8$ is —$C(O)R^{20}$, and $R^{20}$ is selected from $C_{1-6}$ alkyl, $C_{3-10}$ carbocyclyl, $C_{6-10}$ aryl, 3-10 membered cycloheteroalkyl, 5-10 membered heteroaryl, and —$(CH_2)_q$—$R^{28}$. In certain embodiments, $R^{20}$ is $(CH_2)_q$—$R^{28}$, and $R^{28}$ is selected from $C_{3-10}$ carbocyclyl, $C_{6-10}$ aryl, 3-10 membered cycloheteroalkyl, and 5-10 membered heteroaryl. In certain embodiments, $R^{20}$ is $(CH_2)_q$—$R^{28}$, and $R^{28}$ is —$NR^{32}R^{33}$. In certain embodiments, $R^{32}$ and $R^{33}$ each independently is selected from H, $C_{1-6}$ alkyl, and $C_{7-12}$ aralkyl.

In certain embodiments, $R^8$ is —$C(O)OR^{21}$. In certain embodiments, $R^{21}$ is selected from $C_{1-6}$ alkyl and —$(CH_2)_q$—$R^{28}$. In certain embodiments, $R^{28}$ is selected from $C_{6-10}$ aryl and 5-10 membered heteroaryl.

In certain embodiments, $R^8$ is —$C(O)NR^{22}R^{23}$. In certain embodiments, $R^{22}$ and $R^{23}$ each independently is selected from H, $C_{1-6}$ alkyl, and —$(CH_2)_r$—$R^{29}$. In certain embodiments, $R^{29}$ is selected from $C_{6-10}$ aryl and 5-10 membered heteroaryl.

In certain embodiments, $R^8$ is —$S(O)_2R^{24}$. In certain embodiments, $R^{24}$ is selected from $C_{1-6}$ alkyl, $C_{6-10}$ aryl, 5-10 membered heteroaryl, and —$(CH_2)_r$—$R^{39}$.

In certain embodiments, $R^8$ is —$(CH_2)_p$—$R^{25}$. In certain embodiments, $R^{25}$ is selected from $C_{6-10}$ aryl and 5-10 membered heteroaryl.

In certain embodiments, $X^1$ is $CR^6R^7$ and $X^2$ is $NR^8$.

In certain embodiments, n is 1 and $X^3$ is $CR^{12}R^{13}$. In certain embodiments, $R^{12}$ is H and $R^{13}$ is H. However, in certain embodiments, there is no $X^3$ (i.e., wherein n is 0).

In certain embodiments, the compound is selected from:

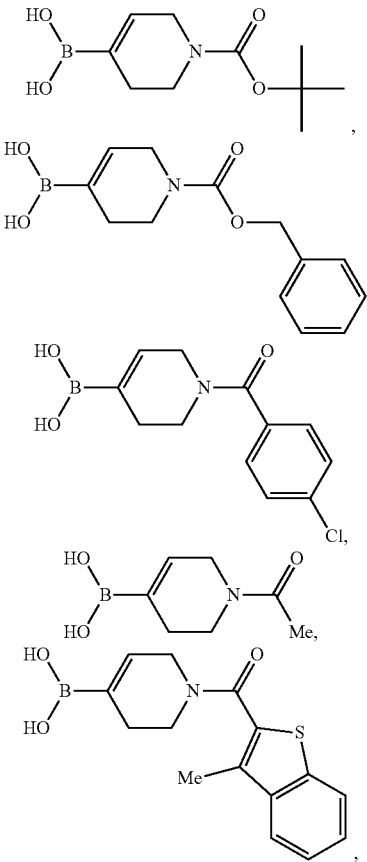

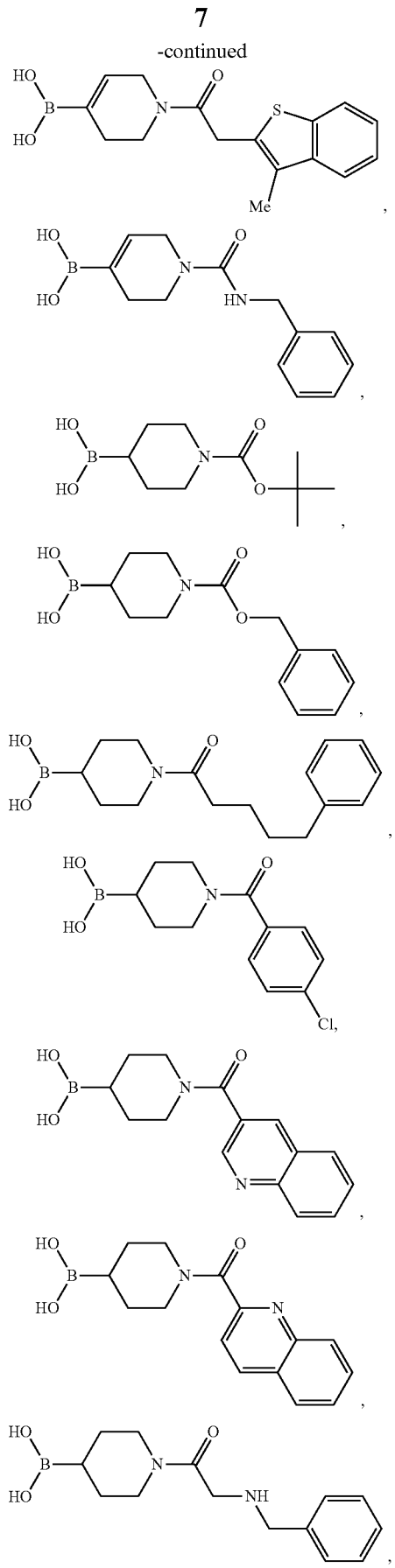

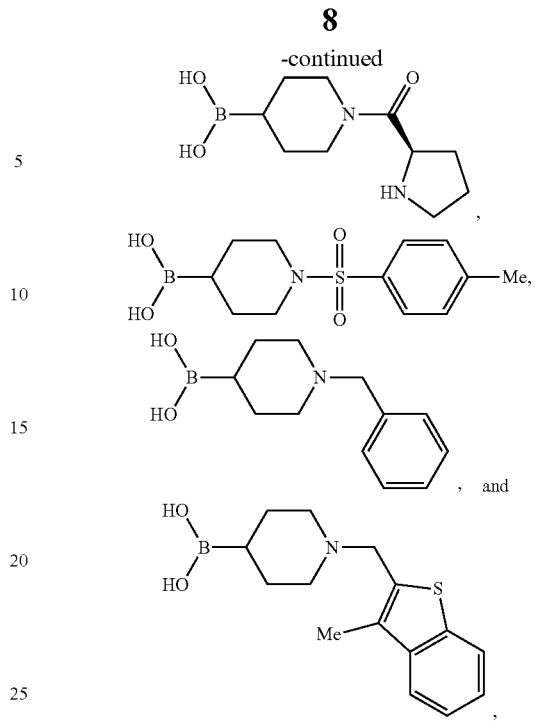

or a pharmaceutically acceptable salt, solvate or prodrug thereof, or mixture thereof.

In another aspect, provided herein are pharmaceutical compositions comprising a compound of the present invention or a pharmaceutically acceptable salt, solvate or prodrug thereof, or mixture thereof, and a pharmaceutically acceptable excipient.

In yet another aspect, provided herein are methods of treating an FAAH-mediated disorder comprising administering to a subject in need thereof a therapeutically effective amount of a compound of the present invention or a pharmaceutically acceptable salt, solvate or prodrug thereof, or mixture thereof, or a pharmaceutical composition thereof.

In certain embodiments, the FAAH-mediated disorder is selected from a painful disorder, an inflammatory disorder, an immune disorder, depression, anxiety, an anxiety-related disorder, a sleep disorder, a feeding behavior, a movement disorder, glaucoma, neuroprotection and cardiovascular disease.

In certain embodiments, the FAAH-mediated disorder is a painful disorder. In certain embodiments, the painful disorder is selected from neuropathic pain, central pain, deafferentiation pain, chronic pain, stimulus of nociceptive receptors, acute pain, non-inflammatory pain, inflammatory pain, pain associated with cancer, preoperative pain, arthritic pain, lumbosacral pain, musculo-skeletal pain, headache, migraine, muscle ache, lower back and neck pain, and toothache. In certain embodiments, the painful disorder is neuropathic pain. In certain embodiments, the painful disorder is arthritic pain. In certain embodiments, the arthritic pain is osteoarthritic pain. In certain embodiments, the arthritic pain is rheumatoid arthritic pain. In certain embodiments, the inflammatory pain is associated with an inflammatory disorder.

In certain embodiments, the FAAH-mediated disorder is an inflammatory disorder. In certain embodiments, the inflammatory disorder is irritable bowel disease.

DETAILED DESCRIPTION

Provided are inhibitors of FAAH that contain at least one Lewis acidic boron head group, such as a boronic acid, boronic ester, borinic acid or borinic ester head group. Such compounds include compounds of formula I or a pharmaceutically acceptable salt, solvate, or prodrug thereof, or a mixture thereof:

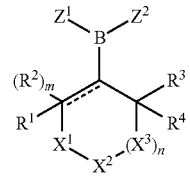

wherein:
- - - - - is selected from a single bond and a double bond;
m is 1 when - - - - - is a single bond;
m is 0 when - - - - - is a double bond;
$X^1$ is selected from $NR^5$ and $CR^6R^7$;
$X^2$ is selected from $NR^8$ and $CR^9R^{10}$;
$X^3$ is selected from $NR^{11}$ and $CR^{12}R^{13}$;
n is 0 or 1;
provided that at least one of $X^1$, $X^2$ and $X^3$ is selected from $NR^5$, $NR^8$ or $NR^{11}$;
$Z^1$ is selected from $-OR^{14}$ and $C_{1-6}$ alkyl;
$Z^2$ is selected from $-OR^{15}$ and $C_{1-6}$ alkyl;
or alternatively, $Z^1$ and $Z^2$, together with the boron atom to which they are bound, form a 5- to 8-membered ring having at least one O atom directly attached to the boron atom, wherein the ring is comprised of carbon atoms and optionally one or more additional heteroatoms independently selected from the group consisting of N, S, and O;
$R^1$, $R^2$, $R^3$, $R^4$, $R^6$, $R^7$, $R^9$, $R^{10}$, $R^{12}$ and $R^{13}$ each independently is selected from H, halogen, $C_{1-6}$ alkyl, $C_{2-6}$ alkenyl, $C_{2-6}$ alkynyl, $C_{1-6}$ perhaloalkyl, $-CN$, $-OR^{16}$, $NR^{17}R^{18}$, $-C(O)R^{19}$, $C_{3-10}$ carbocyclyl, $C_{6-10}$ aryl, $C_{7-12}$ aralkyl, 3-10 membered heterocyclyl, and 5-10 membered heteroaryl;
$R^5$, $R^8$ and $R^{11}$ each independently is selected from H, $C_{1-6}$ alkyl, $C_{2-6}$ alkenyl, $C_{2-6}$ alkynyl, $-C(O)R^{20}$, $-C(O)OR^{21}$, $-C(O)NR^{22}R^{23}$, $S(O)_2R^{24}$, $C_{3-10}$ carbocyclyl, $C_{6-10}$ aryl, 3-10 membered heterocyclyl, 5-10 membered heteroaryl, and $-(CH_2)_p-R^{25}$;
$R^{14}$ and $R^{15}$, at each occurrence, each independently is selected from H, $C_{1-6}$ alkyl, $C_{2-6}$ alkenyl, and $C_{2-6}$ alkynyl;
$R^{16}$, at each occurrence, each independently is selected from H, $C_{1-6}$ alkyl, $C_{2-6}$ alkenyl, $C_{2-6}$ alkynyl, $C_{3-10}$ carbocyclyl, $C_{6-10}$ aryl, $C_{7-12}$ aralkyl, 3-10 membered heterocyclyl, and 5-10 membered heteroaryl;
$R^{17}$ and $R^{18}$, at each occurrence, each independently is selected from H, $C_{1-6}$ alkyl, $C_{2-6}$ alkenyl, $C_{2-6}$ alkynyl, $-C(O)R^{26}$, $-C(O)OR^{27}$, $C_{3-10}$ carbocyclyl, $C_{6-10}$ aryl, $C_{7-12}$ aralkyl, 3-10 membered heterocyclyl, and 5-10 membered heteroaryl;
$R^{19}$, at each occurrence, each independently is selected from $C_{1-6}$ alkyl, $C_{2-6}$ alkenyl, $C_{2-6}$ alkynyl, $C_{3-10}$ carbocyclyl, $C_{6-10}$ aryl, $C_{7-12}$ aralkyl, 3-10 membered heterocyclyl, and 5-10 membered heteroaryl;
$R^{20}$ and $R^{21}$ each independently is selected from $C_{1-6}$ alkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl, and $-(CH_2)_q-R^{28}$;
$R^{22}$ and $R^{23}$ each independently is selected from H, $C_{1-6}$ alkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl, and $-(CH_2)_r-R^{29}$;
$R^{24}$ is selected from $C_{1-6}$ alkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl, and $-(CH_2)_t-R^{30}$;
$R^{25}$ is selected from $C_{3-10}$ carbocyclyl, $C_{6-10}$ aryl, 3-10 membered heterocyclyl, and 5-10 membered heteroaryl;
$R^{26}$ and $R^{27}$ each independently is selected from $C_{1-6}$ alkyl, $C_{2-6}$ alkenyl, $C_{2-6}$ alkynyl, $C_{3-10}$ carbocyclyl, $C_{6-10}$ aryl, $C_{7-12}$ aralkyl, 3-10 membered heterocyclyl, and 5-10 membered heteroaryl;
$R^{28}$, $R^{29}$, and $R^{30}$, at each occurrence, each independently is selected from $-OR^{31}$, $-NR^{32}R^{33}$, $C_{3-10}$ carbocyclyl, $C_{6-10}$ aryl, 3-10 membered heterocyclyl, and 5-10 membered heteroaryl;
$R^{31}$, $R^{32}$ and $R^{33}$, at each occurrence, each independently is selected from H, $C_{1-6}$ alkyl, $C_{2-6}$ alkenyl, $C_{2-6}$ alkynyl, $C_{3-10}$ carbocyclyl, $C_{6-10}$ aryl, $C_{7-12}$ aralkyl, 3-10 membered heterocyclyl, and 5-10 membered heteroaryl; and
p, q, r, and t, at each occurrence, is independently selected from 1, 2, 3, 4, 5 and 6.

In some embodiments, $X^2$ is $NR^8$ and $X^1$ is $CR^6R^7$, i.e., compounds of the formula II:

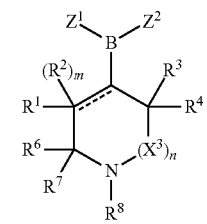

or a pharmaceutically acceptable salt, solvate or prodrug thereof or mixture thereof, wherein - - - - - $Z^1$, $Z^2$, $R^1$, $R^2$, $R^3$, $R^4$, $R^6$, $R^7$, $R^8$, $X^3$, n and m are as defined above and herein. In certain preferred embodiments, $Z^1$ and $Z^2$ are both OH.

Embodiments of compounds of formula II include compounds of formula III (i.e., wherein n is 1 and $X^3$ is $CR^{12}R^{13}$):

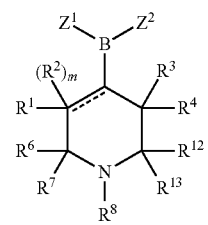

or a pharmaceutically acceptable salt, solvate or prodrug thereof, or mixture thereof, wherein - - - - - $Z^1$, $Z^2$, $R^1$, $R^2$, $R^3$, $R^4$, $R^6$, $R^7$, $R^8$, $R^{12}$, $R^{13}$ and m are as defined above and herein. In certain preferred embodiments, $Z^1$ and $Z^2$ are both OH.

Formula II also encompasses compounds of the formulae IIIa or IIIb:

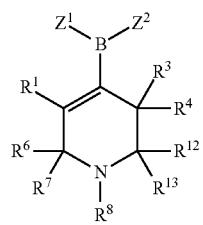

-continued

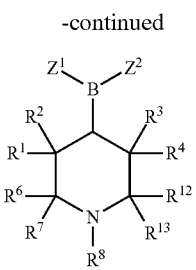

IIIb or a pharmaceutically acceptable salt, solvate or prodrug thereof, or mixture thereof, wherein $Z^1$, $Z^2$, $R^1$, $R^2$, $R^3$, $R^4$, $R^6$, $R^7$, $R^8$, $R^{12}$ and $R^{13}$ are as defined above and herein. In certain preferred embodiments, $Z^1$ and $Z^2$ are both OH.

Other embodiments of compounds of formula II include compounds of formula IV (i.e., wherein n is 0):

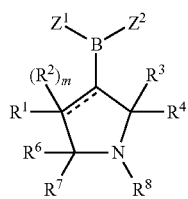

IV or a pharmaceutically acceptable salt, solvate or prodrug thereof, or mixture thereof, wherein ----- $Z^1$, $Z^2$, $R^1$, $R^2$, $R^3$, $R^4$, $R^6$, $R^7$, $R^8$ and m are as defined above and herein. In certain preferred embodiments, $Z^1$ and $Z^2$ are both OH.

Formula IV also encompasses compounds of the formulae IVa or IVb:

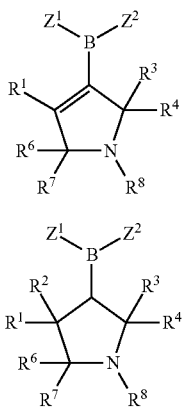

IVa

IVb or a pharmaceutically acceptable salt, solvate or prodrug thereof, or mixture thereof, wherein $Z^1$, $Z^2$, $R^1$, $R^2$, $R^3$, $R^4$, $R^6$, $R^7$, $R^8$ and m are as defined above and herein. In certain preferred embodiments, $Z^1$ and $Z^2$ are both OH.

In some embodiments of compounds having any of formulae II, III, IIIa, IIIb, IV, IVa, and IVb, $R^8$ is not H. In certain embodiments, $R^8$ is not —$CH^3$. In certain embodiments, $R^8$ is selected from $C_{1-6}$ alkyl, —$C(O)R^{20}$, —$C(O)OR^{21}$, —$C(O)NR^{22}R^{23}$, $S(O)_2R^{24}$, and —$(CH_2)_p$—$R^{25}$.

In some embodiments wherein $R^8$ is —$C(O)R^{20}$, $R^{20}$ is selected from $C_{1-6}$ alkyl, $C_{3-10}$ carbocyclyl, $C_{6-10}$ aryl, 3-10 membered heterocyclyl, 5-10 membered heteroaryl, and —$(CH_2)_q$—$R^{28}$.

In some embodiments, wherein $R^8$ is —$C(O)R^{20}$, $R^{20}$ is —$(CH_2)_q$—$R^{28}$, and $R^{28}$ is selected from $C_{3-10}$ carbocyclyl, $C_{6-10}$ aryl, 3-10 membered heterocyclyl, and 5-10 membered heteroaryl. In some embodiments, q is 1 or 2 and $R^{28}$ is $C_{6-10}$ aryl or 5-10 membered heteroaryl. In some embodiments, q is 3 or 4 and $R^{28}$ is $C_{6-10}$ aryl or 5-10 membered heteroaryl. In some embodiments, $R^{28}$ is phenyl. In other embodiments, $R^{28}$ is 5-10 membered heteroaryl (e.g., pyridyl, indolyl, benzofuranyl or benzothiophenyl).

In some embodiments, wherein $R^8$ is —$C(O)R^{20}$, $R^{20}$ is —$(CH_2)_q$—$R^{28}$, and $R^{28}$ is —$NR^{32}R^{33}$. In some embodiments, each of $R^{32}$ and $R^{33}$ is independently selected from H, $C_{1-6}$ alkyl, and $C_{7-12}$ aralkyl. In certain embodiments, q is 1 or 2. In certain embodiments, or q is 1. In some embodiments, one of $R^{32}$ and $R^{33}$ is H and the other is $C_{1-6}$ alkyl or $C_{7-12}$ aralkyl (e.g., benzyl). In other embodiments each of $R^{32}$ and $R^{33}$ independently is $C_{1-6}$ alkyl or $C_{7-12}$ aralkyl (e.g., benzyl).

In some embodiments, $R^8$ is —$C(O)OR^{21}$ and $R^{21}$ is selected from $C_{1-6}$ alkyl, $C_{6-10}$ aryl, 5-10 membered heteroaryl, and —$(CH_2)_q$—$R^{28}$. In certain embodiments, q is 1 or 2 and $R^{28}$ is selected from $C_{6-10}$ aryl and 5-10 membered heteroaryl. In some embodiments, $R^{21}$ is benzyl (i.e., q is 1 and $R^{28}$ is phenyl).

In some embodiments, $R^8$ is —$C(O)NR^{22}R^{23}$ and $R^{22}$ and $R^{23}$ each independently is selected from H, $C_{1-6}$ alkyl, and —$(CH_2)_r$—$R^{29}$. In certain embodiments, r is 1 or 2. In certain embodiments, r is 1. In some embodiments, $R^{29}$ is $C_{6-10}$ aryl or 5-10 membered heteroaryl. In some embodiments, $R^{29}$ is phenyl. In some embodiments, one of $R^{22}$ and $R^{23}$ is H and the other is $C_{1-6}$ alkyl or —$(CH_2)_r$—$R^{29}$. In other embodiments, each of $R^{22}$ and $R^{23}$ independently is $C_{1-6}$ alkyl or —$(CH_2)_r$—$R^{29}$. In some embodiments, —$(CH_2)_r$—$R^{29}$ is benzyl (i.e., r is 1 and $R^{29}$ is phenyl).

In some embodiments, $R^8$ is —$S(O)_2R^{24}$ and $R^{24}$ is selected from $C_{1-6}$ alkyl, $C_{6-10}$ aryl, 5-10 membered heteroaryl, and —$(CH_2)_r$—$R^{39}$. In certain embodiments, $R^{24}$ is phenyl.

In some embodiments, $R^8$ is —$(CH_2)_p$—$R^{25}$ and $R^{25}$ is selected from $C_{6-10}$ aryl and 5-10 membered heteroaryl. In some embodiments, p is 1 or 2. In certain embodiments, p is 1. In certain embodiments, $R^{25}$ is phenyl. In other embodiments, $R^{25}$ is 5-10 membered heteroaryl (e.g., pyridyl, indolyl, benzofuranyl or benzothiophenyl).

In some embodiments of compounds having any of formulae II, III, IIIa, IIIb, IV, IVa, and IVb, each of $R^3$ and $R^4$ is H or $C_{1-6}$ alkyl. In some embodiments, each of $R^3$ and $R^4$ is H.

In some embodiments of compounds having any of formulae II, III, IIIa, IIIb, IV, IVa, and IVb, each of $R^6$ and $R^7$ is H or $C_{1-6}$ alkyl. In some embodiments, each of $R^6$ and $R^7$ is H.

In some embodiments of compounds of formula II wherein n is 1 and $X^3$ is $CR^{12}R^{13}$ (i.e., compounds of any of formulae III, IIIa, and IIIb) each of $R^{12}$ and $R^{13}$ is H or $C_{1-6}$ alkyl. In some embodiments, each of $R^{12}$ and $R^{13}$ is H.

In some embodiments of compounds of formula II, III or IV wherein ----- is a double bond and m is 0 (i.e., compounds of formulae IIIa or IVa), $R^1$ is H or $C_{1-6}$ alkyl. In some embodiments, $R^1$ is H.

In some embodiments of compounds of formula II, III or IV wherein ----- is a single bond and m is 1 (i.e., compounds of formulae IIIb or IVb), each of $R^1$ and $R^2$ is H or $C_{1-6}$ alkyl. In some embodiments, each of $R^1$ and $R^2$ is H.

In some embodiments of compounds of formula II, ----- is a double bond; m is 0; $X^1$ is $CR^6R^7$, $X^2$ is $NR^8$; n is 1; $X^3$ is $CR^{12}R^{13}$; and each of $R^1$, $R^3$, $R^4$, $R^6$, $R^7$, $R^{12}$ and $R^{13}$ is H. In other embodiments, ----- is a single bond; m is 1; $X^1$ is $CR^6R^7$, $X^2$ is $NR^8$; n is 1; $X^3$ is $CR^{12}R^{13}$; and each of $R^1$, $R^2$, $R^3$, $R^4$, $R^6$, $R^7$, $R^{12}$ and $R^{13}$ is H.

In some embodiments, $X^1$ is $NR^5$ and $X^2$ is $CR^9R^{10}$, i.e., compounds having the formula V:

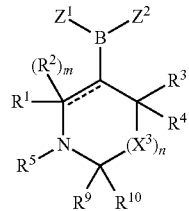

V or a pharmaceutically acceptable salt, solvate or prodrug thereof, or mixture thereof, wherein ----- $Z^1, Z^2, R^1, R^2, R^3, R^4, R^5, R^9, R^{10}, X^3$, n and m are as defined above and herein. In certain preferred embodiments, $Z^1$ and $Z^2$ are both OH.

Embodiments of compounds of formula V include compounds of formula VI (i.e., wherein n is 1 and $X^3$ is $CR^{12}R^{13}$):

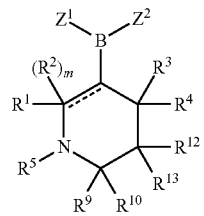

VI or a pharmaceutically acceptable salt, solvate or prodrug thereof, or mixture thereof, wherein ----- $Z^1, Z^2, R^1, R^2, R^3, R^4, R^5, R^9, R^{10}, R^{12}, R^{13}$ and m are as defined above and herein. In certain preferred embodiments, $Z^1$ and $Z^2$ are both OH.

Formula VI also encompasses compounds of the formula VIa or VIb:

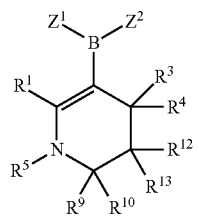

VIa

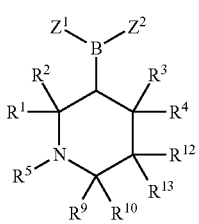

VIb or a pharmaceutically acceptable salt, solvate or prodrug thereof, or mixture thereof, wherein $Z^1, Z^2, R^1, R^2, R^3, R^4, R^5, R^9, R^{10}, R^{12}$ and $R^{13}$ are as defined above and herein. In certain preferred embodiments, $Z^1$ and $Z^2$ are both OH.

Other embodiments of compounds of formula V include compounds of formula VII (i.e., wherein n is 0):

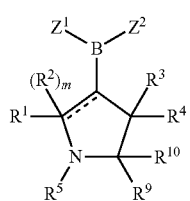

VII or a pharmaceutically acceptable salt, solvate or prodrug thereof, or mixture thereof, wherein ----- $Z^1, Z^2, R^1, R^2, R^3, R^4, R^5, R^9, R^{10}$ and m are as defined above and herein. In certain preferred embodiments, $Z^1$ and $Z^2$ are both OH.

Formula VII also encompasses compounds of the formulae VIIa or VIIb:

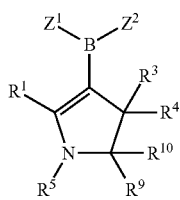

VIIa

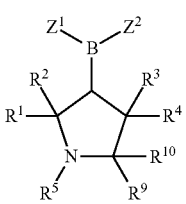

VIIb or a pharmaceutically acceptable salt, solvate or prodrug thereof, or mixture thereof, wherein $Z^1, Z^2, R^1, R^2, R^3, R^4, R^5, R^9$ and $R^{19}$ are as defined above and herein. In certain preferred embodiments, $Z^1$ and $Z^2$ are both OH.

In embodiments of compounds having any of formulae V, VI, VIa, VIb, VII, VIIa, and VIIb, $R^5$ is not H. In certain embodiments, $R^5$ is not $-CH^3$. In certain embodiments, $R^5$ is selected from $C_{1-6}$ alkyl, $-C(O)R^{20}$, $-C(O)OR^{21}$, $-C(O)NR^{22}R^{23}$, $S(O)_2R^{24}$, and $-(CH_2)_p-R^{25}$.

In some embodiments wherein $R^5$ is $-C(O)R^{20}$, $R^{20}$ is selected from $C_{1-6}$ alkyl, $C_{3-10}$ carbocyclyl, $C_{6-10}$ aryl, 3-10 membered heterocyclyl, 5-10 membered heteroaryl, and $-(CH_2)_q-R^{28}$.

In some embodiments, wherein $R^5$ is $-C(O)R^{20}$, $R^{20}$ is $-(CH_2)_q-R^{28}$, and $R^{28}$ is selected from $C_{3-10}$ carbocyclyl, $C_{6-10}$ aryl, 3-10 membered heterocyclyl, and 5-10 membered heteroaryl. In some embodiments, q is 1 or 2 and $R^{28}$ is $C_{6-10}$ aryl or 5-10 membered heteroaryl. In some embodiments, q is 3 or 4 and $R^{28}$ is $C_{6-10}$ aryl or 5-10 membered heteroaryl. In some embodiments, $R^{28}$ is phenyl. In other embodiments, $R^{28}$ is 5-10 membered heteroaryl (e.g., pyridyl, indolyl, benzofuranyl or benzothiophenyl).

In some embodiments, wherein $R^5$ is $-C(O)R^{20}$, $R^{20}$ is $-(CH_2)_q-R^{28}$, and $R^{28}$ is $-NR^{32}R^{33}$. In some embodiments, $R^{32}$ and $R^{33}$ each independently is selected from H, $C_{1-6}$ alkyl, and $C_{7-12}$ aralkyl. In certain embodiments, q is 1 or 2. In certain embodiments, q is 1. In some embodiments, one of $R^{32}$ and $R^{33}$ is H and the other is $C_{1-6}$ alkyl or $C_{7-12}$ aralkyl (e.g., benzyl). In other embodiments each of $R^{32}$ and $R^{33}$ independently is $C_{1-6}$ alkyl or $C_{7-12}$ aralkyl (e.g., benzyl).

In some embodiments, $R^5$ is —C(O)O$R^{21}$ and $R^{21}$ is selected from $C_{1-6}$ alkyl and —(CH$_2$)$_q$—$R^{28}$. In certain embodiments, q is 1 or 2 and $R^{28}$ is selected from $C_{6-10}$ aryl and 5-10 membered heteroaryl. In some embodiments, $R^{21}$ is benzyl.

In some embodiments, $R^5$ is —C(O)N$R^{22}R^{23}$ and $R^{22}$ and $R^{23}$ each independently is selected from H, $C_{1-6}$ alkyl, and —(CH$_2$)$_r$—$R^{29}$. In certain embodiments, r is 1 or 2. In certain embodiments, r is 1. In some embodiments, $R^{29}$ is $C_{6-10}$ aryl or 5-10 membered heteroaryl. In some embodiments, $R^{29}$ is phenyl. In some embodiments, one of $R^{22}$ and $R^{23}$ is H and the other is $C_{1-6}$ alkyl or —(CH$_2$)$_r$—$R^{29}$. In other embodiments, each of $R^{22}$ and $R^{23}$ independently is $C_{1-6}$ alkyl or —(CH$_2$)$_r$—$R^{29}$. In some embodiments, —(CH$_2$)$_r$—$R^{29}$ is benzyl (i.e., r is 1 and $R^{29}$ is phenyl).

In some embodiments, $R^5$ is —S(O)$_2R^{24}$ and $R^{24}$ is selected from $C_{1-6}$ alkyl, $C_{6-10}$ aryl, 5-10 membered heteroaryl, and —(CH$_2$)$_t$—$R^{39}$. In certain embodiments, $R^{24}$ is phenyl.

In some embodiments, $R^5$ is —(CH$_2$)$_p$—$R^{25}$ and $R^{25}$ is selected from $C_{6-10}$ aryl and 5-10 membered heteroaryl. In some embodiments, p is 1 or 2, or p is 1. In certain embodiments, $R^{25}$ is phenyl. In other embodiments, $R^{25}$ is 5-10 membered heteroaryl (e.g., pyridyl, indolyl, benzofuranyl or benzothiophenyl).

In certain embodiments of compounds having any of formulae V, VI, VIa, VIb, VII, VIIa, and VIIb, each of $R^3$ and $R^4$ is H or $C_{1-6}$ alkyl. In some embodiments, each of $R^3$ and $R^4$ is H.

In certain embodiments of compounds having any of formulae V, VI, VIa, VIb, VII, VIIa, and VIIb, each of $R^9$ and $R^{10}$ is H or $C_{1-6}$ alkyl. In some embodiments, each of $R^9$ and $R^{10}$ is H.

In some embodiments of compounds of formula V wherein n is 1 and $X^3$ is C$R^{12}R^{13}$ (i.e., compounds of any of formulae VI, VIa, and VIb) each of $R^{12}$ and $R^{13}$ is H or $C_{1-6}$ alkyl. In some embodiments, each of $R^{12}$ and $R^{13}$ is H.

In some embodiments of compounds of formula V, VI or VII wherein ----- is a double bond and m is 0 (i.e., compounds of formulae VIIa or VIIa), $R^1$ is H or $C_{1-6}$ alkyl. In some embodiments, $R^1$ is H.

In some embodiments of compounds of formula V, VI or VII, wherein ----- is a single bond and m is 1 (i.e., compounds of formulae VIIb or VIIb), each of $R^1$ and $R^2$ is H or $C_{1-6}$ alkyl. In some embodiments, each of $R^1$ and $R^2$ is H.

In some embodiments of compounds of formula V, ----- is a double bond; m is 0; $X^1$ is N$R^8$; $X^2$ is C$R^9R^{10}$; n is 1; $X^3$ is C$R^{12}R^{13}$; and each of $R^1$, $R^3$, $R^4$, $R^9$, $R^{10}$, $R^{12}$ and $R^{13}$ is H. In other embodiments, ----- is a single bond; m is 1; $X^1$ is N$R^8$; $X^2$ is C$R^9R^{10}$; n is 1; $X^3$ is C$R^{12}R^{13}$; and each of $R^1$, $R^2$, $R^3$, $R^4$, $R^9$, $R^{10}$, $R^{12}$ and $R^{13}$ is H.

In some embodiments, $X^1$ is C$R^6R^7$, $X^2$ is C$R^9R^{10}$, and $X^3$ is N$R^{11}$, i.e., compounds of the formula VIII:

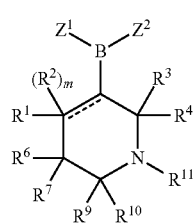

VIII or a pharmaceutically acceptable salt, solvate or prodrug thereof, or mixture thereof, wherein ----- $Z^1$, $Z^2$, $R^1$, $R^2$, $R^3$, $R^4$, $R^6$, $R^7$, $R^9$, $R^{10}$, $R^{11}$ and m are as defined above and herein. In certain preferred embodiments, $Z^1$ and $Z^2$ are both OH. Formula VIII also encompasses compounds of the formulae VIIIa or VIIIb:

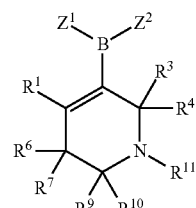

VIIIa

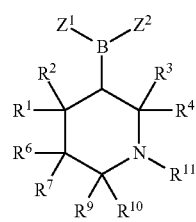

VIIIb or a pharmaceutically acceptable salt, solvate or prodrug thereof, or mixture thereof, wherein $Z^1$, $Z^2$, $R^1$, $R^2$, $R^3$, $R^4$, $R^6$, $R^7$, $R^9$, $R^{10}$ and $R^{11}$ are as defined above and herein. In certain preferred embodiments, $Z^1$ and $Z^2$ are both OH.

In some embodiments of compounds having any of formulae VIII, VIIIa, and VIIIb, $R^{11}$ is not H. In certain embodiments, $R^{11}$ is not —CH$^3$. $R^{11}$ is selected from $C_{1-6}$ alkyl, —C(O)$R^{20}$, —C(O)O$R^{21}$, —C(O)N$R^{22}R^{23}$, S(O)$_2^{24}$, and —(CH$_2$)$_p$—$R^{25}$.

In some embodiments wherein $R^{11}$ is —C(O)$R^{20}$, $R^{20}$ can be selected from $C_{1-6}$ alkyl, $C_{3-10}$ carbocyclyl, $C_{6-10}$ aryl, 3-10 membered heterocyclyl, 5-10 membered heteroaryl, and —(CH$_2$)$_q$—$R^{28}$.

In some embodiments, wherein $R^{11}$ is —C(O)$R^{20}$, $R^{20}$ is —(CH$_2$)$_q$—$R^{28}$, and $R^{28}$ is selected from $C_{3-10}$ carbocyclyl, $C_{6-10}$ aryl, 3-10 membered heterocyclyl, and 5-10 membered heteroaryl. In some embodiments, q is 1 or 2 and $R^{28}$ is $C_{6-10}$ aryl or 5-10 membered heteroaryl. In some embodiments, q is 3 or 4 and $R^{28}$ is $C_{6-10}$ aryl or 5-10 membered heteroaryl. In some embodiments, $R^{28}$ is phenyl. In other embodiments, $R^{28}$ is 5-10 membered heteroaryl (e.g., pyridyl, indolyl, benzofuranyl or benzothiophenyl).

In some embodiments, wherein $R^{11}$ is —C(O)$R^{20}$, $R^{20}$ is —(CH$_2$)$_q$—$R^{28}$, and $R^{28}$ is —N$R^{32}R^{33}$. In some embodiments, $R^{32}$ and $R^{33}$ each independently is selected from H, $C_{1-6}$ alkyl, and $C_{7-12}$ aralkyl. In certain embodiments, q is 1 or 2, or q is 1. In some embodiments, one of $R^{32}$ and $R^{33}$ is H and the other is $C_{1-6}$ alkyl or $C_{7-12}$ aralkyl (e.g., benzyl). In other embodiments each of $R^{32}$ and $R^{33}$ independently is $C_{1-6}$ alkyl or $C_{7-12}$ aralkyl (e.g., benzyl).

In some embodiments, $R^{11}$ is —C(O)O$R^{21}$ and $R^{21}$ is selected from $C_{1-6}$ alkyl and —(CH$_2$)$_q$—$R^{28}$. In certain embodiments, q is 1 or 2 and $R^{28}$ is selected from $C_{6-10}$ aryl and 5-10 membered heteroaryl. In some embodiments, $R^{21}$ is benzyl.

In some embodiments, $R^{11}$ is —C(O)N$R^{22}R^{23}$ and $R^{22}$ and $R^{23}$ each independently is selected from H, $C_{1-6}$ alkyl, and —(CH$_2$)$_r$—$R^{29}$. In certain embodiments, r is 1 or 2. In certain embodiments, r is 1. In some embodiments, $R^{29}$ is $C_{6-10}$ aryl or 5-10 membered heteroaryl. In some embodiments, $R^{29}$ is phenyl. In some embodiments, one of $R^{22}$ and $R^{23}$ is H and the other is $C_{1-6}$ alkyl or —$(CH_2)_r$—$R^{29}$. In other embodiments, each of $R^{22}$ and $R^{23}$ independently is $C_{1-6}$ alkyl or —$(CH_2)_r$—$R^{29}$. In some embodiments, —$(CH_2)_r$—$R^{29}$ is benzyl (i.e., r is 1 and $R^{29}$ is phenyl).

In some embodiments, $R^{11}$ is —$S(O)_2R^{24}$ and $R^{24}$ is selected from $C_{1-6}$ alkyl, $C_{6-10}$ aryl, 5-10 membered heteroaryl, and —$(CH_2)_t$—$R^{30}$. In certain embodiments, $R^{24}$ is phenyl.

In some embodiments, $R^{11}$ is —$(CH_2)_p$—$R^{25}$ and $R^{25}$ is selected from $C_{6-10}$ aryl and 5-10 membered heteroaryl. In some embodiments, p is 1 or 2. In certain embodiments, p is 1. In certain embodiments, $R^{25}$ is phenyl. In other embodiments, $R^{25}$ is 5-10 membered heteroaryl (e.g., pyridyl, indolyl, benzofuranyl or benzothiophenyl).

In certain embodiments of compounds having any of formulae VIII, VIIIa, and VIIIb, each of $R^3$ and $R^4$ is H or $C_{1-6}$ alkyl. In some embodiments, each of $R^3$ and $R^4$ is H.

In certain embodiments of compounds having any of formulae VIII, VIIIa, and VIIIb, each of $R^6$ and $R^7$ is H or $C_{1-6}$ alkyl. In some embodiments, each of $R^6$ and $R^7$ is H.

In certain embodiments of compounds having any of formulae VIII, VIIIa, and VIIIb, each of $R^9$ and $R^{19}$ is H or $C_{1-6}$ alkyl. In some embodiments, each of $R^9$ and $R^{19}$ is H.

In embodiments of compounds of formula VIII wherein ----- is a double bond and m is 0 (i.e., compounds of formula VIIIa), $R^1$ is H or $C_{1-6}$ alkyl. In some embodiments, $R^1$ is H.

In embodiments of compounds of formula VIII wherein ----- is a single bond and m is 1 (i.e., compounds of formula VIIIb), each of $R^1$ and $R^2$ is H or $C_{1-6}$ alkyl. In some embodiments, each of $R^1$ and $R^2$ is H.

In some embodiments of compounds of formula VIII, ----- is a double bond; m is 0; $X^1$ is $CR^6R^7$; $X^2$ is $CR^9R^{10}$; n is 1; $X^3$ is $NR^{11}$; and each of $R^1$, $R^3$, $R^4$, $R^6$, $R^7$, $R^9$ and $R^{10}$ is H. In other embodiments, ----- is a single bond; m is 1; $X^1$ is $CR^6R^7$; $X^2$ is $CR^9R^{10}$; n is 1; $X^3$ is $NR^{11}$; and each of $R^1$, $R^2$, $R^3$, $R^4$, $R^6$, $R^7$, $R^9$ and $R^{10}$ is H.

In some embodiments of compounds of formulae I, II, III, IIIa, IIIb, IV, IVa, IVb, V, VI, VIa, VIb, VII, VIIa, VIIb, VIII, VIIIa, or VIIIb, $Z^1$ is —$OR^{14}$ and $Z^2$ is —$OR^{15}$. In certain embodiments $R^{14}$ is H and $R^{15}$ is H.

In other embodiments, $Z^1$ and $Z^2$ taken together with the boron atom to which they are bound, form a 5- to 8-membered ring having at least one O, S, N or $NR^A$ atom directly attached to the boron atom, wherein $R^A$ is selected from hydrogen, —$SO_2R^B$, —$SOR^B$, —$C(O)R^B$, —$CO_2R^B$, —$C(O)N(R^B)_2$, $C_{1-8}$ alkyl, $C_{2-6}$ alkenyl, $C_{2-8}$ alkynyl, $C_{3-10}$ carbocyclyl, 3-10 membered heterocyclyl, $C_{6-10}$ aryl, and 5-10 membered heteroaryl; and each instance of $R^B$ is, independently, $C_{1-6}$ alkyl, $C_{2-6}$ alkenyl, $C_{2-6}$ alkynyl, $C_{3-10}$ carbocyclyl, 3-10 membered heterocyclyl, $C_{6-10}$ aryl, or 5-10 membered heteroaryl. In some embodiments, the 5- to 8-membered ring is with one or more groups selected from halogen, oxo (=O), —$SO_2R^C$, —$SOR^C$, —$C(O)R^C$, —$C(O)OR^C$, —$C(O)N(R^C)_2$, —$C(O)$NHR^C$, $C_{1-6}$ alkyl, $C_{2-6}$ alkenyl, $C_{2-6}$ alkynyl, $C_{3-10}$ carbocyclyl, 3-10 membered heterocyclyl, $C_{6-10}$ aryl, or 5-10 membered heteroaryl groups, or two groups present on the ring are joined to form a 5- to 8-membered monocylic or bicyclic ring optionally containing one or more heteroatoms selected from O, S, N or $NR^A$; wherein each instance of $R^C$ is independently, $C_{1-6}$ alkyl, $C_{2-6}$ alkenyl, $C_{2-6}$ alkynyl, $C_{3-10}$ carbocyclyl, 3-10 membered heterocyclyl, $C_{6-10}$ aryl, or 5-10 membered heteroaryl.

For example, in certain embodiments, $Z^1$ and $Z^2$, taken together with the boron atom to which they are bound, form an optionally substituted 5-membered ring having at least one O, S or $NR^A$ atom directly attached to the boron atom. Exemplary 5-membered rings include, but are not limited to:

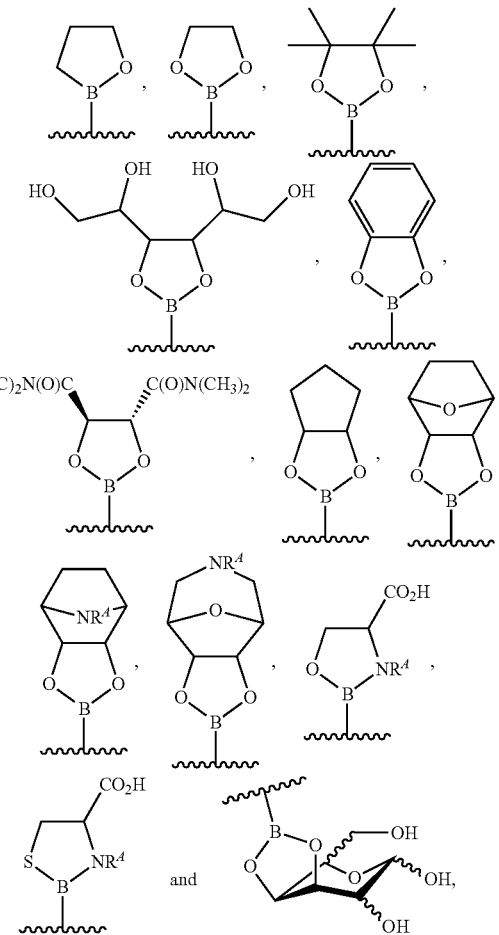

wherein $R^A$ is as defined herein.

In other embodiments, $Z^1$ and $Z^2$, taken together with the boron atom to which they are bound, form a 6-membered ring having at least one O, S or $NR^A$ atom directly attached to the boron atom. Exemplary 6-membered rings include, but are not limited to:

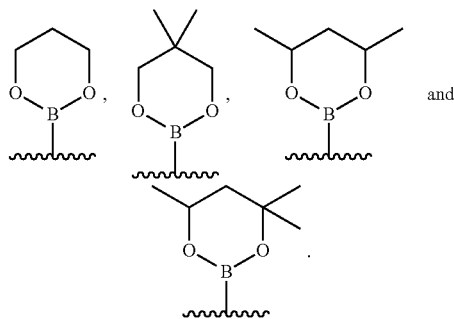

In yet other embodiments, $Z^1$ and $Z^2$ form an 8-membered ring having at least one O, S or $NR^A$ atom directly attached to the boron atom. Exemplary 8-membered ring structures include, but are not limited to:

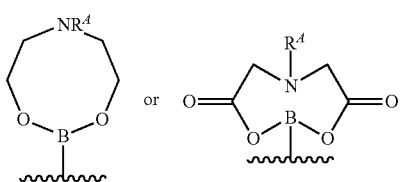

wherein $R^A$ is as defined herein.

In certain embodiments, a compound of formula I or a subset thereof (e.g., a compound of formulae II, III, IIIa, IIIb, V, VI, VIa, VIb, VIII, VIIIa, or VIIIb) is not any one of the following compounds:

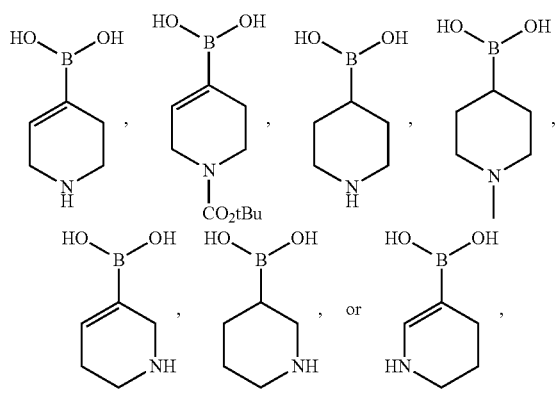

or a pharmaceutically acceptable salt, solvate or prodrug thereof, or mixture thereof.

In certain embodiments, a compound of formula I or a subset thereof (e.g., a compound of formulae IV, IVa, IVb, VII, VIIa or VIIb) is not any one of the following compounds:

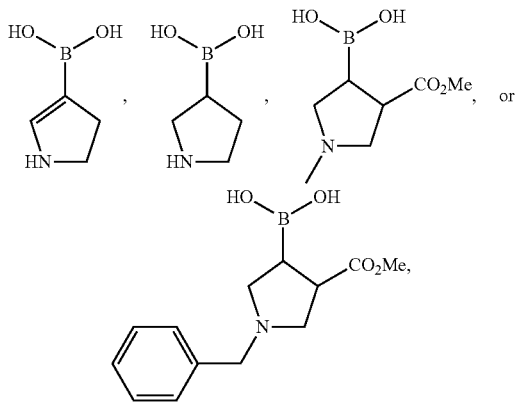

or a pharmaceutically acceptable salt, solvate or prodrug thereof, or mixture thereof.

DEFINITIONS

Definitions of specific functional groups and chemical terms are described in more detail below. The chemical elements are identified in accordance with the Periodic Table of the Elements, CAS version, Handbook of Chemistry and Physics, 75th Ed inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987.

Certain compounds of the present invention can comprise one or more asymmetric centers, and thus can exist in various isomeric forms, e.g., enantiomers and/or diastereomers. The compounds provided herein can be in the form of an individual enantiomer, diastereomer or geometric isomer, or can be in the form of a mixture of stereoisomers, including racemic mixtures and mixtures enriched in one or more stereoisomer. In certain embodiments, the compounds of the invention are enantiopure compounds. In certain other embodiments, mixtures of stereoisomers are provided.

Furthermore, certain compounds, as described herein can have one or more double bonds that can exist as either the cis or trans, or the E or Z isomer, unless otherwise indicated. The invention additionally encompasses the compounds as individual isomers substantially free of other isomers, and alternatively, as mixtures of various isomers, e.g., racemic mixtures of E/Z isomers or mixtures enriched in one E/Z isomer.

Where a particular enantiomer is preferred, it can be provided substantially free of the corresponding enantiomer, i.e., optically enriched. "Optically-enriched," as used herein, means that the compound is made up of a greater proportion of one enantiomer compared to the other. In certain embodiments the compound is made up of at least about 90% by weight of a preferred enantiomer. In other embodiments the compound is made up of at least about 95%, 98%, or 99% by weight of a preferred enantiomer. Preferred enantiomers can be isolated from mixtures by methods known to those skilled in the art, including chiral high pressure liquid chromatography (HPLC) and the formation and crystallization of chiral salts; or preferred enantiomers can be prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); and Wilen, S. H. *Tables of Resolving Agents and Optical Resolutions* p. 268 (E. L. Eliel, Ed., Univ. of Notre Dame Press, Notre Dame, Ind. 1972).

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein a "direct bond" or "covalent bond" refers to a single bond.

As used herein, the term "boronic acid" refers to any chemical compound comprising a —B(OH)$_2$ moiety. Arylboronic acid compounds readily form oligomeric anhydrides by dehydration of the boronic acid moiety (see, for example, Snyder et al., *J. Am. Chem. Soc.* (1958) 80: 3611). Thus, unless otherwise apparent from context, the term "boronic acid" is expressly intended to encompass free boronic acids, oligomeric anhydrides, including, but not limited to, dimers, trimers, and tetramers, and mixtures thereof.

The terms "borinic ester", "borinic acid" and "borinic ester" are art understood terms referring to a —B(OR)$_2$ moiety, a —B(R)OH moiety and a —B(R)OR moiety, respectively, wherein R is a group other than hydrogen (e.g., an $C_{1-6}$ alkyl, $C_{2-6}$ alkenyl, $C_{2-6}$ alkynyl, carbocycyl, heterocycyl, aryl, or heteroaryl group; or two R groups are joined to form a 5- to 8-membered ring optionally containing 1 to 4 heteroatoms).

As used herein, alone or as part of another group, "halo" and "halogen" refer to fluorine (fluoro, —F), chlorine (chloro, —Cl), bromine (bromo, —Br), or iodine (iodo, —I).

As used herein, alone or as part of another group, "alkyl" refers to a monoradical of a straight-chain or branched saturated hydrocarbon group having from 1 to 8 carbon atoms ("$C_{1-8}$ alkyl"). In some embodiments, an alkyl group can have from 1 to 6 carbon atoms ("$C_{1-6}$ alkyl"). In some embodiments, an alkyl group can have from 1 to 4 carbon atoms ("$C_{1-4}$ alkyl"). Examples of $C_{1-4}$ alkyl groups include methyl, ethyl, propyl, isopropyl, butyl, isobutyl, sec-butyl and tert butyl. Examples of $C_{1-6}$ alkyl groups include the aforementioned $C_{1-4}$ alkyl groups as well as pentyl, isopentyl, neopentyl, hexyl and the like. Additional examples of alkyl groups include heptyl, octyl and the like. Unless otherwise specified, each instance of an alkyl group is independently unsubstituted or substituted with 1-5 groups as described below.

As used herein, alone or as part of another group, "alkenyl" refers to a monoradical of a straight-chain or branched hydrocarbon group having from 2 to 8 carbon atoms and one or more carbon-carbon double bonds ("$C_{2-8}$ alkenyl"). In some embodiments, an alkenyl group can have from 2 to 6 carbon atoms ("$C_{2-6}$ alkenyl"). In some embodiments, an alkenyl group can have from 2 to 4 carbon atoms ("$C_{2-4}$ alkenyl"). The one or more carbon-carbon double bonds can be internal (such as in 2-butenyl) or terminal (such as in 1-butenyl). Examples of $C_{2-4}$ alkenyl groups include ethenyl, 1-propenyl, 2-propenyl, 1-butenyl, 2-butenyl, butadienyl and the like. Examples of $C_{2-6}$ alkenyl groups include the aforementioned $C_{2-4}$ alkenyl groups as well as pentenyl, pentadienyl, hexenyl and the like. Additional examples of alkenyl include heptenyl, octenyl, octatrienyl and the like. Unless otherwise specified, each instance of an alkenyl group is independently unsubstituted or substituted with 1-5 groups as described below.

As used herein, alone or as part of another group, "alkynyl" refers to a monoradical of a straight-chain or branched hydrocarbon group having from 2 to 8 carbon atoms and one or more carbon-carbon triple bonds ("$C_{2-8}$ alkynyl"). In some embodiments, an alkynyl group can have from 2 to 6 carbon atoms ("$C_{2-6}$ alkynyl"). In some embodiments, an alkynyl group can have from 2 to 4 carbon atoms ("$C_{2-4}$ alkynyl"). The one or more carbon-carbon triple bonds can be internal (such as in 2-butynyl) or terminal (such as in 1-butynyl). Examples of $C_{2-4}$ alkynyl groups include ethynyl, 1-propynyl, 2-propynyl, 1-butynyl, 2-butynyl and the like. Examples of $C_{2-6}$ alkenyl groups include the aforementioned $C_{2-4}$ alkynyl groups as well as pentynyl, hexynyl and the like. Additional examples of alkynyl include heptynyl, octynyl and the like. Unless otherwise specified, each instance of an alkynyl group is independently unsubstituted or substituted with 1-5 groups as described below.

As used herein, alone or as part of another group, "alkylene" refers to a diradical of a straight-chain or branched saturated alkyl group having from 1 to 6 carbon atoms ("$C_{1-6}$ alkylene"). In some embodiments, an alkylene group can have from 1 to 4 carbon atoms ("$C_{1-4}$ alkylene"). In some embodiments, an alkylene group can have from 1 to 2 carbon atoms ("$C_{1-2}$ alkylene"). Examples of $C_{1-2}$ alkylene groups include methylene and ethylene. Examples of $C_{1-4}$ alkylene groups include the aforementioned $C_{1-2}$ alkylene groups as well as trimethylene (1,3-propanediyl), propylene (1,2-propanediyl), tetramethylene (1,4-butanediyl), butylene (1,2-butanediyl), 1,3-butanediyl, 2-methyl-1,3-propanediyl and the like. Examples of $C_{1-6}$ alkylene groups include the aforementioned $C_{1-4}$ alkylene groups as well as pentamethylene (1,5-pentanediyl), pentylene (1,2-pentanediyl), hexamethylene (1,6-hexanediyl), hexylene (1,2-hexanediyl), 2,3-dimethyl-1,4-butanediyl and the like. In some embodiments, an alkylene group is an α,ω-diradical. Examples of α,ω-diradical alkylene groups include methylene, ethylene, trimethylene, tetramethylene, pentamethylene and hexamethylene. Unless otherwise specified, each instance of an alkylene group is independently unsubstituted or substituted with 1-5 groups as described below.

As used herein, alone or as part of another group, "alkenylene" refers to a diradical of a straight-chain or branched alkenyl having from 2 to 6 carbon atoms and one or more carbon-carbon double bonds ("$C_{2-6}$ alkenylene"). In some embodiments, an alkenylene group can have from 2 to 4 carbon atoms ("$C_{2-4}$ alkenylene"). In some embodiments, an alkenylene group can have 2 carbon atoms, i.e., ethenediyl. The one or more carbon-carbon double bonds can be internal (such as in 1,4-but-2-enediyl) or terminal (such as in 1,4-but-1-enediyl). Examples of $C_{2-4}$ alkenylene groups include ethenediyl, 1,2-propenediyl, 1,3-propenediyl, 1,4-but-1-enediyl, 1,4-but-2-enediyl and the like. Examples of $C_{2-6}$ alkenylene groups include the aforementioned $C_{2-4}$ alkenylene groups as well as 1,5-pent-1-enediyl, 1,4-pent-2-enediyl, 1,6-hex-2-enediyl, 2,5-hex-3-enediyl, 2-methyl-1,4-pent-2-enediyl and the like. In some embodiments, an alkenylene group is an α,ω-diradical. Examples of α,ω-diradical alkenylene groups include ethenediyl, 1,3-propenediyl, 1,4-but-2-enediyl, 1,5-pent-1-enediyl, 1,6-hex-3-enediyl and the like. Unless otherwise specified, each instance of an alkenylene group is independently unsubstituted or substituted with 1-5 groups as described below.

As used herein, alone or as part of another group, "alkynylene" refers to a diradical of a straight-chain or branched alkynyl group having from 2 to 6 carbon atoms and one or more carbon-carbon triple bonds ("$C_{2-6}$ alkynylene"). In some embodiments, an alkynylene group can have from 2 to 4 carbon atoms ("$C_{2-4}$ alkynylene"). In some embodiments, an alkynylene group can have 2 carbon atoms, i.e., ethynediyl. The one or more carbon-carbon triple bonds can be internal (such as in 1,4-but-2-ynediyl) or terminal (such as in 1,4-but-1-ynediyl). Examples of $C_{2-4}$ alkynylene groups include ethynediyl, propynediyl, 1,4-but-1-ynediyl, 1,4-but-2-ynediyl and the like. Examples of $C_{2-6}$ alkynylene groups include the aforementioned $C_{2-4}$ alkynylene groups as well as 1,5-pent-1-ynediyl, 1,4-pent-2-ynediyl, 1,6-hex-2-ynediyl, 2,5-hex-3-ynediyl, 3-methyl-1,5-hex-1-ynediyl and the like. In some embodiments, an alkynylene group is an α,ω-diradical. Examples of α,ω-diradical alkynylene groups include ethynediyl, propynediyl, 1,4-but-2-ynediyl, 1,5-pent-1-ynediyl, 1,6-hex-3-ynediyl and the like. Unless otherwise specified, each instance of an alkynylene group is independently unsubstituted or substituted with 1-5 groups as described below.

As used herein, alone or as part of another group, "perhaloalkyl" refers to an alkyl group having from 1 to 6 carbon atoms, wherein all of the hydrogen atoms are each independently replaced with fluoro or chloro. In some embodiments, all of the hydrogen atoms are each replaced with fluoro. In some embodiments, all of the hydrogen atoms are each replaced with chloro. Examples of perhaloalkyl groups include —$CF_3$, —$CF_2CF_3$, —$CF_2CF_2CF_3$, —$CCl_3$, —$CFCl_2$, —$CF_2Cl$ and the like.

As used herein, alone or as part of another group, "alkoxy" or "alkyloxy" refers to a —O-alkyl group having from 1 to 8 carbon atoms ("$C_{1-8}$ alkoxy"). In some embodiments, an alkoxy group can have from 1 to 6 carbon atoms ("$C_{1-6}$ alkoxy"). In some embodiments, an alkoxy group can have from 1 to 4 carbon atoms ("$C_{1-4}$ alkoxy"). Examples of $C_{1-4}$ alkoxy groups include methoxy, ethoxy, propoxy, isopropoxy, butoxy, tert-butoxy and the like. Examples of $C_{1-6}$ alkoxy group include the aforementioned $C_{1-4}$ alkoxy groups as well as pentyloxy, isopentyloxy, neopentyloxy, hexyloxy and the like. Additional examples of alkoxy groups include heptyloxy, octyloxy and the like. Unless otherwise specified, each instance of an alkoxy group is independently unsubstituted or substituted with 1-5 groups as described below.

As used herein, alone or as part of another group, "perhaloalkoxy" refers to an alkoxy group having from 1 to 3 carbon atoms, wherein all of the hydrogen atoms are each independently replaced with fluoro or chloro. In some embodiments, all of the hydrogen atoms are each replaced with fluoro. In some embodiments, all of the hydrogen atoms are each replaced with chloro. Examples of perhaloalkoxy groups include —$OCF_3$, —$OCF_2CF_3$, —$OCF_2CF_2CF_3$, —$OCCl_3$, —$OCFCl_2$, —$OCF_2Cl$ and the like.

As used herein, alone or as part of another group, "alkylthio" refers to an —S-alkyl group having from 1 to 8 carbon atoms. In some embodiments, an alkylthio group can have from 1 to 6 carbon atoms. In some embodiments, an alkylthio group can have from 1 to 4 carbon atoms. Examples of $C_{1-4}$ alkylthio groups include methylthio, ethylthio, propylthio, isopropylthio, butylthio, isobutylthio and the like. Examples of $C_{1-6}$ alkylthio groups include the aforementioned $C_{1-4}$ alkylthio groups as well as pentylthio, isopentylthio, hexylthio and the like. Additional examples of alkylthio groups include heptylthio, octylthio and the like. Unless otherwise specified, each instance of an alkylthio group is independently unsubstituted or substituted with 1-5 groups as described below.

As used herein, alone or as part of another group, "carbocyclyl" or "carbocycle" refers to a radical of a non-aromatic cyclic hydrocarbon group having from 3 to 10 ring carbon atoms ("$C_{3-10}$ carbocyclyl"). In some embodiments, a carbocyclyl group can have from 3 to 8 ring carbon atoms ("$C_{3-8}$ carbocyclyl"). In some embodiments, a carbocyclyl group can have from 3 to 6 ring carbon atoms ("$C_{3-6}$ carbocyclyl"). Examples of $C_{3-6}$ carbocyclyl groups include cyclopropyl, cyclobutyl, cyclopentyl, cyclopentenyl, cyclohexyl, cyclohexenyl, cyclohexadienyl and the like. Examples of $C_{3-8}$ carbocyclyl groups include the aforementioned $C_{3-6}$ carbocyclyl groups as well as cycloheptyl, cycloheptadienyl, cycloheptatrienyl, cyclooctyl, bicyclo[2.2.1]heptanyl, bicyclo[2.2.2]octanyl and the like. Examples of $C_{3-10}$ carbocyclyl groups include the aforementioned $C_{3-8}$ carbocyclyl groups as well as octahydro-1H-indenyl, decahydronaphthalenyl, spiro[4.5]decanyl and the like. As the foregoing examples illustrate, in some embodiments a carbocyclyl group can be monocyclic ("monocyclic carbocyclyl") or bicyclic ("bicyclic carbocyclyl", e.g., containing a fused, bridged or spiro ring system), and can be saturated or can contain one or more carbon-carbon double or triple bonds. "Carbocyclyl" also refers to a phenyl group (as defined below) fused to a monocyclic carbocyclyl group. Examples of such carbocyclyl groups include 1,2,3,4-tetrahydronaphthalene (e.g., 1,2,3,4-tetrahydronaphthalen-1-yl, 1,2,3,4-tetrahydronaphthalen-5-yl, and the like), 2,3-dihydro-1H-indene (e.g., 2,3-dihydro-1H-inden-1-yl, 2,3-dihydro-1H-inden-4-yl, and the like), indene (e.g., 1H-inden-1-yl, 1H-inden-7-yl, and the like), 5,6,7,8-tetrahydroquinoline (e.g., 5,6,7,8-tetrahydroquinolin-5-yl, 5,6,7,8-tetrahydroquinolin-2-yl, and the like), 4,5,6,7-tetrahydro-1H-indole (e.g., 4,5,6,7-tetrahydro-1H-indol-4-yl, 4,5,6,7-tetrahydro-1H-indol-3-yl, and the like), 4,5,6,7-tetrahydrobenzofuran (e.g., 4,5,6,7-tetrahydrobenzofuran-7-yl, 4,5,6,7-tetrahydrobenzofuran-2-yl, and the like) and the like. Unless otherwise specified, each instance of a carbocyclyl or carbocycle group is independently unsubstituted or substituted with 1-5 groups as described below.

In some embodiments, "carbocyclyl" or "carbocycle" can refer to a monocyclic, saturated carbocyclyl group ("cycloalkyl") having from 3 to 10 ring carbon atoms ("$C_{3-10}$ cycloalkyl"). In some embodiments, a cycloalkyl group can have from 3 to 6 ring carbon atoms ("$C_{3-6}$ cycloalkyl"). In some embodiments, a cycloalkyl group can have from 5 to 6 ring carbon atoms ("$C_{5-6}$ cycloalkyl"). Examples of $C_{5-6}$ cycloalkyl groups include cyclopentyl and cyclohexyl. Examples of $C_{3-6}$ cycloalkyl groups include the aforementioned $C_{5-6}$ cycloalkyl groups as well as cyclopropyl and cyclobutyl. Examples of $C_{3-8}$ cycloalkyl groups include the aforementioned $C_{3-6}$ cycloalkyl groups as well as cycloheptyl and cyclooctyl. Unless otherwise specified, each instance of a cycloalkyl group is independently unsubstituted or substituted with 1-5 groups as described below.

As used herein, alone or as part of another group, "heterocyclyl" or "heterocycle" refers to a radical of a 3- to 10-membered non-aromatic ring system having ring carbon atoms and 1 to 4 ring heteroatoms, each heteroatom independently selected from nitrogen, oxygen and sulfur. In some embodiments, a heterocyclyl group can have from 3 to 7 ring atoms selected from carbon atoms and 1 to 3 heteroatoms, each heteroatom independently selected from nitrogen, oxygen and sulfur. In some embodiments, a heterocyclyl group can have from 5 to 7 ring atoms selected from carbon atoms and 1 or 2 heteroatoms, each heteroatom independently selected from nitrogen, oxygen and sulfur. In some embodiments, a heterocyclyl group can have from 5 to 6 ring atoms selected from carbon atoms and 1 to 3 heteroatoms, each heteroatom independently selected from nitrogen, oxygen and sulfur. Heterocyclyl groups can be saturated or can contain one or more carbon-carbon double bonds, carbon-nitrogen double bonds, or carbon-carbon triple bonds. In heterocyclyl groups that contain one or more nitrogen atoms, the point of attachment can be a carbon or nitrogen atom, as valency permits.

Examples of heterocyclyl groups with 1-2 ring heteroatoms include oxiranyl, aziridinyl, oxetanyl, azetidinyl, pyrrolidinyl, dihydropyrrolyl, tetrahydrofuranyl, dihydrofuranyl, tetrahydrothiophenyl, dihydrothiophenyl, pyrazolidinyl, imidazolidinyl, oxazolidinyl, isoxazolidinyl, thiazolidinyl, piperidinyl, tetrahydropyridinyl, dihydropyridinyl, piperazinyl, tetrahydropyranyl, dioxanyl, morpholinyl, azepanyl, diazepanyl, diazepinyl, oxepanyl, dioxepanyl, oxazepanyl, oxazepinyl and the like. Examples of heterocyclyl groups with 1-3 heteroatoms include the aforementioned heterocyclyl groups as well as triazolidinyl, oxadiazolidinyl, triazinanyl and the like. Heterocyclyl groups can be monocyclic ("monocyclic heterocyclyl") as in the aforementioned examples, bicyclic ("bicyclic heterocyclyl"), or tricyclic ("tricyclic heterocyclyl"). Bicyclic heterocyclyl groups can include one or more heteroatoms in one or both rings. Examples of such bicyclic heterocyclyl groups include tetrahydroindolyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole and the like.

"Heterocyclyl" or "heterocycle" also refers to a radical of a 5- to 10-membered fused ring system having ring carbon atoms and 1 to 4 ring heteroatoms, each heteroatom independently selected from nitrogen, oxygen and sulfur, wherein one ring is aromatic and the other is non-aromatic. In some embodiments, at least one heteroatom is present in either the aromatic or non-aromatic ring, while in other embodiments, at least one heteroatom is present in both rings. In heterocyclyl groups that contain one or more nitrogen atoms, the point of attachment can be a carbon or nitrogen atom, as valency permits. Examples of such heterocyclyl groups include indolinyl (e.g., indolin-1-yl, indolin-4-yl, and the like), isoindolinyl (e.g., isoindolin-1-yl, isoindolin-4-yl, and the like), 4,5,6,7-tetrahydro-1H-indolyl (e.g., tetrahydro-1H-indol-2-yl, 4,5,6,7-tetrahydro-1H-indol-4-yl, and the like), dihydrobenzofuranyl (e.g., dihydrobenzofuran-3-yl, dihydrobenzofuran-5-yl, and the like), 4,5,6,7-tetrahydrobenzofuranyl (e.g., 4,5,6,7-tetrahydrobenzofuran-2-yl, 4,5,6,7-tetrahydrobenzofuran-5-yl, and the like), dihydrobenzothienyl (e.g., dihydrobenzothien-2-yl, dihydrobenzothien-4-yl, and the like), 4,5,6,7-tetrahydrobenzothiophenyl (e.g., 4,5,6,7-tetrahydrobenzothiophen-2-yl, 4,5,6,7-tetrahydrobenzothiophen-7-yl, and the like), 1,2,3,4-tetrahydroquinolinyl (e.g., 1,2,3,4-tetrahydroquinolin-1-yl, 1,2,3,4-tetrahydroquinolin-7-yl, and the like), chromanyl (e.g., chroman-2-yl, chroman-5-yl, and the like), chromenyl (chromen-4-yl, chromen-8-yl, and the like), thiochromanyl (e.g., thiochroman-3-yl, isochroman-7-yl, and the like), 1H-benzo[e][1,4]diazepinyl (e.g., 1H-benzo[e][1,4]diazepin-2-yl, 1H-benzo[e][1,4]diazepin-6-yl, and the like), 2,3-dihydro-1H-pyrrolo[2,3-b]pyridinyl (e.g., 2,3-dihydro-1H-pyrrolo[2,3-b]pyridin-1-yl, 2,3-dihydro-1H-pyrrolo[2,3-b]pyridin-4-yl, and the like), 4,5,6,7-tetrahydro-1H-pyrrolo[2,3-b]pyridinyl (e.g., 4,5,6,7-tetrahydro-1H-pyrrolo[2,3-b]pyridin-2-yl, 4,5,6,7-tetrahydro-1H-pyrrolo[2,3-b]pyridin-4-yl, and the like), 1,4,5,7-tetrahydropyrano[3,4-b]pyrrolyl (e.g., 1,4,5,7-tetrahydropyrano[3,4-b]pyrrol-2-yl, 1,4,5,7-tetrahydropyrano[3,4-b]pyrrol-4-yl, and the like), 2,3-dihydrofuro[2,3-b]pyridinyl (e.g., 2,3-dihydrofuro[2,3-b]pyridin-3-yl, 2,3-dihydrofuro[2,3-b]pyridin-5-yl, and the like), 4,5,6,7-tetrahydrofuro[3,2-c]pyridinyl (e.g., 4,5,6,7-tetrahydrofuro[3,2-c]pyridin-2-yl, 4,5,6,7-tetrahydrofuro[3,2-c]pyridin-5-yl, and the like), 4,5,6,7-tetrahydrothieno[3,2-b]pyridinyl (e.g., 4,5,6,7-tetrahydrothieno[3,2-b]pyridin-2-yl, 4,5,6,7-tetrahydrothieno[3,2-b]pyridin-7-yl, and the like), 5,6-dihydro-4H-furo[3,2-b]pyrrolyl (e.g., 5,6-dihydro-4H-furo[3,2-b]pyrrol-6-yl, 5,6-dihydro-4H-furo[3,2-b]pyrrol-2-yl, and the like), 6,7-dihydro-5H-furo[3,2-b]pyranyl (e.g., 6,7-dihydro-5H-furo[3,2-b]pyran-2-yl, 6,7-dihydro-5H-furo[3,2-b]pyran-6-yl, and the like), 5,7-dihydro-4H-thieno[2,3-c]pyranyl (e.g., 5,7-dihydro-4H-thieno[2,3-c]pyran-2-yl, 5,7-dihydro-4H-thieno[2,3-c]pyran-4-yl, and the like), 1,2,3,4-tetrahydro-1,6-naphthyridinyl (e.g., 1,2,3,4-tetrahydro-1,6-naphthyridin-3-yl, 1,2,3,4-tetrahydro-1,6-naphthyridin-8-yl, and the like), and the like.

Unless otherwise specified, each instance of a heterocyclyl group is independently unsubstituted or substituted with 1-5 groups as described below.

As used herein, alone or as part of another group, "aryl" refers to a radical of an aromatic monocyclic or bicyclic ring system having 6 or 10 ring carbon atoms. Examples of such aryl groups include phenyl, 1-naphthyl and 2-naphthyl. Unless otherwise specified, each instance of an aryl group is independently unsubstituted or substituted with 1-5 groups as described below.

The term "aralkyl" refers to an alkyl group substituted by an aryl group, wherein the alkyl and aryl portions independently are as described below.

As used herein, alone or as part of another group, "heteroaryl" refers to a radical of a 5- to 10-membered aromatic ring system having ring carbon atoms and 1 to 4 ring heteroatoms, each heteroatom independently selected from nitrogen, oxygen and sulfur. Examples of such heteroaryl groups include pyrrolyl, furanyl (furyl), thiophenyl (thienyl), pyrazolyl, imidazolyl, oxazolyl, isoxazolyl, thiazolyl, triazolyl, oxadiazolyl, thiadiazolyl, tetrazolyl, pyridinyl (pyridyl), pyridazinyl, pyrimdinyl, pyrazinyl, triazinyl, indolyl, benzofuranyl, benzothiophenyl (benzothienyl), indazolyl, benzimidazolyl, benzoxazolyl, benzisoxazolyl, benzothiazolyl, quinolinyl, isoquinolinyl, cinnolinyl, quinazolinyl, quinoxalinyl, phthalazinyl, naphthyridinyl and the like. As the foregoing examples illustrate, in some embodiments a heteroaryl group can be monocyclic ("monocyclic heteroaryl"), and in some embodiments a heteroaryl group can be bicyclic ("bicyclic heteroaryl"). For bicyclic heteroaryl groups wherein one ring does not contain a heteroatom (e.g., indolyl, quinolinyl, and the like) the point of attachment can be on either ring, i.e., either the ring bearing a heteroatom (e.g., 2-indolyl) or the ring that does not contain a heteroatom (e.g., 5-indolyl). Unless otherwise specified, each instance of a heteroaryl group is independently unsubstituted or substituted with 1-5 groups as described below.

The term "heteroaralkyl" refers to an alkyl group substituted by a heteroaryl group, wherein the alkyl and heteroaryl portions independently are as described below.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, alkyl, alkenyl, alkynyl, alkylene, alkenylene, alkynylene, alkoxy, alkylthio, carbocycle, heterocycle, aryl, aralkyl, heteroaryl, and heteroaralkyl groups as described above and herein are substituted or unsubstituted (i.e., optionally substituted). In general, the term "substituted", whether preceded by the term "optionally" or not, means that one or more hydrogens of the designated moiety are replaced with a suitable substituent. Unless otherwise indicated, a substituted group can have a suitable substituent at each substitutable position of the group, and when more than one position in any given structure is substituted with more than one substituent, then the substituent can be either the same or different at these positions. Combinations of substituents envisioned by this invention are preferably those that result in the formation of stable compounds. The term "stable", as used herein, refers to compounds that are not substantially altered when subjected to conditions to allow for their production, detection, and, in certain embodiments, their recovery, purification, and/or use for one or more of the purposes disclosed herein.

Suitable monovalent substituents on a carbon atom are independently halogen; —$(CH_2)_{0-4}R^\circ$; —$(CH_2)_{0-4}OR^\circ$; —O—$(CH_2)_{0-4}C(O)OR^\circ$; —$(CH_2)_{0-4}$—CH$(OR^\circ)_2$; —$(CH_2)_{0-4}SR^\circ$; —$(CH_2)_{0-4}$Ph, which can be substituted with one or more $R^\circ$; —$(CH_2)_{0-4}O(CH_2)_{0-1}$Ph which can be substituted with $R^\circ$; —CH=CHPh, which can be substituted with one or more $R^\circ$; —$NO_2$; —CN; —$N_3$; —$(CH_2)_{0-4}N(R^\circ)_2$; —$(CH_2)_{0-4}N(R^\circ)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$N(R^\circ)N(R^\circ)C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}C(O)SR^\circ$; $(CH_2)_{0-4}C(O)OSiR^\circ_3$; —$(CH_2)_{0-4}OC(O)R^\circ$; —OC(O)$(CH_2)_{0-4}SR^\circ$, —SC(S)SR$^\circ$; —$(CH_2)_{0-4}SC(O)R^\circ$; —$(CH_2)_{0-4}C(O)NR^\circ_2$; —$C(S)NR^\circ_2$; —$C(S)SR^\circ$; —SC(S)SR$^\circ$, —$(CH_2)_{0-4}OC(O)NR^\circ_2$; —C(O)N(OR$^\circ$)R$^\circ$; —C(O)C(O)R$^\circ$; —C(O)CH$_2$C(O)R$^\circ$; —C(NOR$^\circ$)R$^\circ$; —$(CH_2)_{0-4}SSR^\circ$; —$(CH_2)_{0-4}S(O)_2R^\circ$; —$(CH_2)_{0-4}S(O)_2OR^\circ$; —$(CH_2)_{0-4}OS(O)_2R^\circ$; —S(O)$_2$NR$^\circ_2$; —$(CH_2)_{0-4}S(O)R^\circ$; —N(R$^\circ$)S(O)$_2$NR$^\circ_2$; —N(R$^\circ$)S(O)$_2$R$^\circ$; —N(OR$^\circ$)R$^\circ$;

—C(NH)NR°$_2$; —P(O)$_2$R°; —P(O)R°$_2$; —OP(O)R°$_2$; —OP(O)(OR°)$_2$; SiR°$_3$; —(C$_{1-4}$ alkylene)O—N(R°)$_2$; or —(C$_{1-4}$ alkylene)C(O)O—N(R°)$_2$, wherein each R° can be substituted as defined below and is independently hydrogen, C$_{1-8}$ alkyl, C$_{2-8}$ alkenyl, C$_{2-8}$ alkynyl, C$_{1-8}$ heteroalkyl, C$_{2-8}$ heteroalkenyl, C$_{2-8}$ heteroalkynyl, —CH$_2$Ph, —O(CH$_2$)$_{0-1}$Ph, or a 5- or 6-membered saturated, partially unsaturated, or aromatic ring having 0-4 heteroatoms independently selected from nitrogen, oxygen, or sulfur; or, notwithstanding the definition above, two independent occurrences of R°, taken together with the atom(s) to which they are bound, form a 3- to 12-membered saturated, partially unsaturated, or aromatic mono- or bicyclic ring having 0-4 heteroatoms independently selected from nitrogen, oxygen, or sulfur, which can be substituted as defined below.

Suitable monovalent substituents on R° (or the ring formed by two independent occurrences of R° together with the atoms to which they are bound), are independently halogen, —(CH$_2$)$_{0-2}$R$^●$, —(CH$_2$)$_{0-2}$OH, —(CH$_2$)$_{0-2}$OR$^●$, —(CH$_2$)$_{0-2}$CH(OR$^●$)$_2$, —CN, —N$_3$, —(CH$_2$)$_{0-2}$C(O)R$^●$, —(CH$_2$)$_{0-2}$C(O)OH, —(CH$_2$)$_{0-2}$C(O)OR$^●$, —(CH$_2$)$_{0-2}$SR$^●$, —(CH$_2$)$_{0-2}$SH, —(CH$_2$)$_{0-2}$NH$_2$, —(CH$_2$)$_{0-2}$NHR$^●$, —(CH$_2$)$_{0-2}$NR$^●_2$, —NO$_2$, —SiR$^●_3$, —OSiR$^●_3$, —C(O)SR$^●$, —(C$_{1-4}$ alkylene)C(O)OR$^●$, or —SSR$^●$ wherein each R$^●$ is unsubstituted or substituted with one or more halogens, and is independently selected from C$_{1-4}$ alkyl, C$_{2-4}$ alkenyl, C$_{2-4}$ alkynyl, —CH$_2$Ph, —O(CH$_2$)$_{0-1}$Ph, or a 5- or 6-membered saturated, partially unsaturated, or aromatic ring having 0-4 heteroatoms independently selected from nitrogen, oxygen, or sulfur. Suitable divalent substituents on a saturated carbon atom of R° include =O and =S.

Suitable divalent substituents on a saturated carbon atom include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen; C$_{1-6}$ alkyl, C$_{2-6}$ alkenyl, C$_{2-6}$ alkynyl, each of which can be substituted as defined below; or an unsubstituted 5- or 6-membered saturated, partially unsaturated, or aromatic ring having 0-4 heteroatoms independently selected from nitrogen, oxygen, or sulfur. Suitable divalent substituents that are bound to vicinal substitutable carbons include: —O(CR*$_2$)$_{2-3}$O—, wherein each independent occurrence of R* is selected from hydrogen; C$_{1-6}$ alkyl, C$_{2-6}$ alkenyl, C$_{2-6}$ alkynyl, each of which can be substituted as defined below; or an unsubstituted 5- or 6-membered saturated, partially unsaturated, or aromatic ring having 0-4 heteroatoms independently selected from nitrogen, oxygen, or sulfur.

Suitable substituents on a C$_{1-6}$ alkyl, C$_{2-6}$ alkenyl, or C$_{2-6}$ alkynyl R* group include halogen, —R$^●$, —(haloR$^●$), —OH, —OR$^●$, —CN, —C(O)OH, —C(O)OR$^●$, —NH$_2$, —NHR$^●$, —NR$^●_2$, or —NO$_2$, wherein each R$^●$ is unsubstituted or substituted with one or more halogens, and is independently C$_{1-4}$ alkyl, C$_{2-4}$ alkenyl, C$_{2-4}$ alkynyl, —CH$_2$Ph, —O(CH$_2$)$_{0-1}$Ph, or a 5- or 6-membered saturated, partially unsaturated, or aromatic ring having 0-4 heteroatoms independently selected from nitrogen, oxygen, or sulfur.

Suitable substituents on a substitutable nitrogen include —R$^†$, —NR$^†_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†_2$, —C(S)NR$^†_2$, —C(NH)NR$^†_2$, or —N(R$^†$)S(O)$_2$R$^†$; wherein each R$^†$ is independently hydrogen; C$_{1-6}$ alkyl, C$_{2-6}$ alkenyl, C$_{2-6}$ alkynyl, each of which can be substituted as defined below; unsubstituted —OPh; or an unsubstituted 5- or 6-membered saturated, partially unsaturated, or aromatic ring having 0-4 heteroatoms independently selected from nitrogen, oxygen, or sulfur; or, notwithstanding the definition above, two independent occurrences of R$^†$, taken together with the atom(s) to which they are bound form an unsubstituted 3- to 12-membered saturated, partially unsaturated, or aromatic mono- or bicyclic ring having 0-4 heteroatoms independently selected from nitrogen, oxygen, or sulfur.

Suitable substituents on a C$_{1-6}$ alkyl, C$_{2-6}$ alkenyl, or C$_{2-6}$ alkynyl R$^†$ group are independently halogen, —R$^●$, —OH, —OR$^●$, —CN, —C(O)OH, —C(O)OR$^●$, —NH$_2$, —NHR$^●$, —NR$^●_2$, or —NO$_2$, wherein each R$^●$ is unsubstituted or substituted with one or more halogens, and is independently C$_{1-4}$ alkyl, C$_{2-4}$ alkenyl, C$_{2-4}$ alkynyl, —CH$_2$Ph, —O(CH$_2$)$_{0-1}$Ph, or a 5- or 6-membered saturated, partially unsaturated, or aromatic ring having 0-4 heteroatoms independently selected from nitrogen, oxygen, or sulfur.

In certain embodiments, each C$_{1-6}$ alkyl, C$_{2-6}$ alkenyl, C$_{2-6}$ alkynyl, C$_{3-10}$ carbocyclyl, C$_{6-10}$ aryl, C$_{7-12}$ aralkyl, 3-10 membered heterocyclyl, and 5-10 membered heteroaryl, alone or as part of another group, is independently and with 1-5 substituents selected from halogen, C$_{1-6}$ alkyl, C$_{2-6}$ alkenyl, C$_{2-6}$ alkynyl, C$_{1-6}$ perhaloalkyl, —OH, C$_{1-6}$ alkoxy, —NH$_2$, —NH(C$_{1-6}$ alkyl), —N(C$_{1-6}$alkyl)$_2$, and —CN.

As used herein, "solvate" refers to a compound of the present invention or a pharmaceutically acceptable salt or prodrug thereof, that further includes a stoichiometric or non-stoichiometric amount of solvent bound by non-covalent intermolecular forces. Where the solvent is water, the solvate is a hydrate.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein, and unless otherwise specified, the term "prodrug" means a biologically active derivative of a compound that can hydrolyze, oxidize, or otherwise react under physiological conditions (in vitro or in vivo) to provide the pharmacologically active compound. Additionally, prodrugs can be converted to the compounds of the invention by chemical or biochemical methods in an ex vivo environment. For example, prodrugs can be slowly converted to the compounds of the invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. Examples of prodrugs include, but are not limited to, compounds that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include compounds that comprise —NO, —NO$_2$, —ONO, or —ONO$_2$ moieties. The compounds of the invention readily undergo dehydration to form oligomeric anhydrides by dehydration of the boronic acid moiety to form dimers, trimers, and tetramers, and mixtures thereof. These oligomeric species hydrolyze under physiological conditions to reform the boronic acid. As such, the oligomeric anhydrides are contemplated as a "prodrug" of the compounds described herein, and can be used in the treatment of disorder and/or conditions a wherein the inhibition of FAAH provides a therapeutic effect.

Exemplary prodrugs of the compounds described herein include, but are not limited to, compounds wherein $Z^1$ and $Z^2$ taken together form a 5- to 8-membered ring having at least one heteroatom atom selected from nitrogen, oxygen and sulfur directly attached to boron, wherein the ring is comprised of carbon atoms and optionally one or more additional heteroatoms independently selected from nitrogen, oxygen and sulfur.

Other examples of prodrugs of the compounds described herein are trifluoroborate prodrugs which hydrolyze to the boronic acid (i.e., —BF$_3$ hydrolyzing to —B(OH)$_2$) at acidic pH. Salt forms of the boronic acid (e.g., Na$^+$, Li$^+$, Mg$^{2+}$, Ca$^{2+}$, and the like) are also considered prodrugs Amino acids can be used to form prodrugs, such as, for example, serine and cysteine protected boronic acids. 1,2 and 1,3 hydroxy sugars can be used to form prodrugs, such as, for example, glycerol, erythritol, threitol, ribitol, arabinitol, xylitol, allitol, altritol, galactitol, sorbitol, mannitol, and iditol protected boronic acids. Other sugars which are useful in the formation of prodrugs include, but are not limited to, maltitol, lactitol, and isomalt; other monosaccharides which include hexoses (e.g., allose, altrose, glucose, mannose, gulose, idose, galactose, talose) and pentoses (e.g., ribose, arabinaose, xylose, lyxose); pentaerythritols and structural derivatives thereof, such as methylated, ethylated, acetate, ethoxylate, and propoxylate derivatives; and phenolic polyols such as 1,2,4 benzenetriol, 5-methyl benzene-1,2,3-triol, 2,3,4-trihydroxybenzaldehyde, and 3,4,5-trihydroxybenzamide. Prodrugs also include NMIDA-derivatives.

Pharmaceutically Acceptable Compositions and Formulations

In certain embodiments, the present invention provides a pharmaceutically acceptable composition comprising a compound of any of formulae I, II, III, IIIa, IIIb, IV, IVa, IVb, V, VI, VIa, VIb, VII, VIIa, VIIb, VIII, VIIIa, and VIIIb, or a pharmaceutically acceptable salt, solvate or prodrug thereof, or mixture thereof, and a pharmaceutically acceptable excipient.

Pharmaceutically acceptable excipients include any and all solvents, diluents or other liquid vehicles, dispersion or suspension aids, surface active agents, isotonic agents, thickening or emulsifying agents, preservatives, solid binders, lubricants and the like, as suited to the particular dosage form desired. General considerations in the formulation and/or manufacture of pharmaceutically acceptable compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21$^{st}$ Edition (Lippincott Williams & Wilkins, 2005).

Pharmaceutically acceptable compositions described herein can be prepared by any method known in the art of pharmacology. In general, such preparatory methods include the steps of bringing the active ingredient into association with an excipient and/or one or more other accessory ingredients, and then, if necessary and/or desirable, shaping and/or packaging the product into a desired single- or multi-dose unit.

Pharmaceutically acceptable compositions can be prepared, packaged, and/or sold in bulk, as a single unit dose, and/or as a plurality of single unit doses. As used herein, a "unit dose" is discrete amount of the pharmaceutically acceptable composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutically acceptable composition of the invention will vary, depending upon the identity, size, and/or condition of the subject treated and further depending upon the route by which the composition is to be administered. By way of example, the composition can comprise between about 0.1% and about 100% (w/w) active ingredient, or between about 2% and about 90% (w/w) active ingredient, or between about 5% and about 80% (w/w) active ingredient.

Pharmaceutically acceptable excipients used in the manufacture of provided pharmaceutically acceptable compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents can also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, etc., and/or combinations thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfate, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for oral and parenteral administration include pharmaceutically acceptable emulsions, microemulsions, solutions, suspensions, syrups and elixirs. In addition to the active ingredients, the liquid dosage forms can comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor, alcohols, oils, modified oils, glycols, polysorbates, cyclodextrins, polymers, and combinations thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form can comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They can optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredients can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose or starch. Such dosage forms can comprise, as is normal practice, additional substances other than inert diluents, e.g., tableting lubricants and other tableting aids such a magnesium stearate and microcrystalline cellulose. In the case of capsules, tablets and pills, the dosage forms can comprise buffering agents. They can optionally comprise opacifying agents and can be of a composition that they release the active ingredient(s) only, or preferentially, in a certain part of the intestinal tract, optionally, in a delayed manner Examples of embedding compositions which can be used include polymeric substances and waxes.

Dosage forms for topical and/or transdermal administration of a compound of this invention can include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as may be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutically acceptable compositions described herein include short needle devices such as those described in U.S. Pat. Nos. 4,886,499; 5,190,521; 5,328,483; 5,527,288; 4,270,537;

5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations can, for example, comprise from about 1% to about 10% (w/w) active ingredient, although the concentration of the active ingredient can be as high as the solubility limit of the active ingredient in the solvent. Formulations for topical administration can further comprise one or more of the additional ingredients described herein.

A pharmaceutically acceptable composition of the invention can be prepared, packaged, and/or sold in a formulation suitable for pulmonary administration via the buccal cavity. Such a formulation can comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions can include a solid fine powder diluent such as sugar and are conveniently provided in a unit dose form.

Low boiling propellants generally include liquid propellants having a boiling point of below 65° F. at atmospheric pressure. Generally the propellant can constitute 50 to 99.9% (w/w) of the composition, and the active ingredient can constitute 0.1 to 20% (w/w) of the composition. The propellant can further comprise additional ingredients such as a liquid non-ionic and/or solid anionic surfactant and/or a solid diluent (which can have a particle size of the same order as particles comprising the active ingredient).

Pharmaceutically acceptable compositions of the invention formulated for pulmonary delivery can provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and can conveniently be administered using any nebulization and/or atomization device. Such formulations can further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration can have an average diameter in the range from about 0.1 to about 200 nanometers.

The formulations described herein as being useful for pulmonary delivery are useful for intranasal delivery of a pharmaceutically acceptable composition of the invention. Another formulation suitable for intranasal administration is a coarse powder comprising the active ingredient and having an average particle from about 0.2 to 500 micrometers. Such a formulation is administered, by rapid inhalation through the nasal passage from a container of the powder held close to the nares.

Formulations suitable for nasal administration can, for example, comprise from about as little as 0.1% (w/w) and as much as 100% (w/w) of the active ingredient, and can comprise one or more of the additional ingredients described herein. A pharmaceutically acceptable composition of the invention can be prepared, packaged, and/or sold in a formulation suitable for buccal administration. Such formulations can, for example, be in the form of tablets and/or lozenges made using conventional methods, and can comprise, for example, 0.1 to 20% (w/w) active ingredient, the balance comprising an orally dissolvable and/or degradable composition and, optionally, one or more of the additional ingredients described herein. Alternately, formulations suitable for buccal administration can comprise a powder and/or an aerosolized and/or atomized solution and/or suspension comprising the active ingredient. Such powdered, aerosolized, and/or aerosolized formulations, when dispersed, can have an average particle and/or droplet size in the range from about 0.1 to about 200 nanometers, and can further comprise one or more of the additional ingredients described herein.

A pharmaceutically acceptable composition of the invention can be prepared, packaged, and/or sold in a formulation suitable for ophthalmic administration. Such formulations can, for example, be in the form of eye drops including, for example, a 0.1/1.0% (w/w) solution and/or suspension of the active ingredient in an aqueous or oily liquid carrier. Such drops can further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

Although the descriptions of pharmaceutically acceptable compositions provided herein are principally directed to pharmaceutical compositions which are suitable for administration to humans, it will be understood by the skilled artisan that such compositions are generally suitable for administration to animals of all sorts. Modification of pharmaceutically acceptable compositions suitable for administration to humans in order to render the compositions suitable for administration to various animals is well understood, and the ordinarily skilled veterinary pharmacologist can design and/or perform such modification with ordinary experimentation.

Also provided are kits comprising one or more compounds of the invention (or pharmaceutically acceptable salts or prodrugs thereof), and/or one or more pharmaceutically acceptable compositions as described herein. Kits are typically provided in a suitable container (e.g., for example, a foil, plastic, or cardboard package). In certain embodiments, a kit can include one or more pharmaceutical excipients, pharmaceutical additives, therapeutically active agents, and the like, as described herein. In certain embodiments, a kit can include means for proper administration, such as, for example, graduated cups, syringes, needles, cleaning aids, and the like. In certain embodiments, a kit can include instructions for proper administration and/or preparation for proper administration.

Methods of Treatment

Provided are methods for treating an FAAH-mediated disorder by administering a therapeutically effective amount of a compound of any of formulae I, II, III, IIIa, IIIb, IV, IVa, IVb, V, VI, VIa, VIb, VII, VIIa, VIIb, VIII, VIIIa, and VIIIb, or a pharmaceutically acceptable salt, solvate or prodrug thereof, or mixture thereof, or a pharmaceutically acceptable salt, solvate or prodrug thereof, or mixture thereofto a subject in need thereof.

Also provided are methods for inhibiting FAAH in a subject by administering a therapeutically effective amount of a compound of any of formulae I, II, III, IIIa, IIIb, IV, IVa, IVb, V, VI, VIa, VIb, VII, VIIa, VIIb, VIII, VIIIa, and VIIIb, or a pharmaceutically acceptable salt, solvate or prodrug thereof, or mixture thereof, to a subject in need thereof.

As used herein, and unless otherwise specified, the terms "treat," "treating" and "treatment" contemplate an action that occurs while a subject is suffering from the specified disease, condition, or disorder, which reduces the severity of the disease or disorder, or retards or slows the progression of the disease or disorder. Treatment can be via prophylactic or therapeutic therapy.

As used herein, and unless otherwise specified, a "therapeutically effective amount" of a compound is an amount sufficient to provide a therapeutic benefit in the treatment or management of a disease, disorder, or condition, or to delay or minimize one or more symptoms associated with the disease, disorder, or condition. A therapeutically effective amount of a compound means an amount of therapeutic agent, alone or in combination with other therapies, which provides a therapeutic benefit in the treatment or management of the disease or condition. The term "therapeutically effective amount" can encompass an amount that improves overall therapy, reduces or avoids symptoms or causes of disease, disorder, or condition, or enhances the therapeutic efficacy of another therapeutic agent. The therapeutically effective amount in a subject will vary depending on the compound, the disease and its severity, and the age, weight, etc., of the subject to be treated. In some embodiments, a "therapeutically effective amount" can encompass a "prophylactically effective amount."

As used herein, and unless otherwise specified, a "prophylactically effective amount" of a compound is an amount sufficient to prevent a disease, disorder, or condition, or one or more symptoms associated with the disease, disorder, or condition, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

As used herein, and unless otherwise specified, the terms "manage," "managing" and "management" encompass preventing the recurrence of the specified disease, disorder, or condition in a subject who has already suffered from the disease or disorder, and/or lengthening the time that a subject who has suffered from the disease, disorder, or condition remains in remission. The terms encompass modulating the threshold, development and/or duration of the disease, disorder or condition, or changing the way that a subject responds to the disease, disorder, or condition.

The term "subject" is defined herein to include animals such as mammals, including, but not limited to, primates (e.g., humans (e.g., male, female, infant, child, adolescant, adult, elderly, etc.)), cows, sheep, goats, horses, dogs, cats, birds, rabbits, rats, mice and the like. In preferred embodiments, the subject is a human.

In other embodiments, the present invention provides a method for inhibiting FAAH in a biological sample comprising the step of contacting said sample with a compound of any of formulae I, II, III, IIIa, IIIb, IV, IVa, IVb, V, VI, VIa, VIb, VII, VIIa, VIIb, VIII, VIIIa, and VIIIb, or a pharmaceutically acceptable salt, solvate or prodrug thereof, or mixture thereof.

The phrases "FAAH-mediated diseases," "FAAH-mediated disorders" and "FAAH-mediated conditions," as used interchangeably, include, but are not limited to, painful conditions, painful diseases or painful disorders, inflammatory disorders, immune disorders, depression, anxiety, anxiety-related disorders, sleep disorders, feeding behaviors, movement disorders, glaucoma, neuroprotection and cardiovascular disease. The terms "disease," "disorder," and "condition" are used interchangeably.

In certain embodiments, the FAAH-mediated disorder is a painful disorder. As used herein, a "painful disorder" includes, but is not limited to, neuropathic pain (e.g., peripheral neuropathic pain), central pain, deafferentiation pain, chronic pain (e.g., chronic nociceptive pain, and other forms of chronic pain such as post-operative pain), stimulus of nociceptive receptors, acute pain (e.g., phantom and transient acute pain), non-inflammatory pain, inflammatory pain, pain associated with cancer, wound pain, burn pain, post-operative pain, pain associated with medical procedures, arthritic pain (e.g., pain associated with rheumatoid arthritis, osteoarthritis), lumbosacral pain, musculo-skeletal pain, headache, migraine, muscle ache, lower back and neck pain, toothache and the like.

In certain embodiments, the painful disorder is neuropathic pain. The term "neuropathic pain" refers to pain resulting from injury to a nerve. Neuropathic pain is distinguished from nociceptive pain, which is the pain caused by acute tissue injury involving small cutaneous nerves or small nerves in muscle or connective tissue. Neuropathic pain typically is long-lasting or chronic and often develops days or months following an initial acute tissue injury. Neuropathic pain can involve persistent, spontaneous pain as well as allodynia, which is a painful response to a stimulus that normally is not painful. Neuropathic pain also can be characterized by hyperalgesia, in which there is an accentuated response to a painful stimulus that usually is trivial, such as a pin prick. Neuropathic pain conditions can develop following neuronal injury and the resulting pain may persist for months or years, even after the original injury has healed. Neuronal injury can occur in the peripheral nerves, dorsal roots, spinal cord or certain regions in the brain. Neuropathic pain conditions include: diabetic neuropathy; sciatica; non-specific lower back pain; multiple sclerosis pain; fibromyalgia; HIV-related neuropathy; neuralgia, such as post-herpetic neuralgia and trigeminal neuralgia; and pain resulting from physical trauma, amputation, cancer, chemotherapy-induced pain, chemotherapy, surgery, invasive medical procedures, toxins burns, infection, or chronic inflammatory conditions. Neuropathic pain can result from a peripheral nerve disorder such as neuroma; nerve compression; nerve crush, nerve stretch or incomplete nerve transsection; mononeuropathy or polyneuropathy. Neuropathic pain can also result from a disorder such as dorsal root ganglion compression; inflammation of the spinal cord; contusion, tumor or hemisection of the spinal cord; tumors of the brainstem, thalamus or cortex; or trauma to the brainstem, thalamus or cortex.

The symptoms of neuropathic pain are heterogeneous and are often described as spontaneous shooting and lancinating pain, or ongoing, burning pain. In addition, there is pain associated with normally non-painful sensations such as "pins and needles" (paraesthesias and dysesthesias), increased sensitivity to touch (hyperesthesia), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

In certain embodiments, the painful disorder is non-inflammatory pain and/or inflammatory pain. The types of non-inflammatory pain include, without limitation, peripheral neuropathic pain (e.g., pain caused by a lesion or dysfunction in the peripheral nervous system), central pain (e.g., pain caused by a lesion or dysfunction of the central nervous system), deafferentation pain (e.g., pain due to loss of sensory input to the central nervous system), chronic nociceptive pain (e.g., certain types of cancer pain), noxious stimulus of nociceptive receptors (e.g., pain felt in response to tissue damage or impending tissue damage), phantom pain (e.g., pain felt in a part of the body that no longer exists, such as a limb that has been amputated), pain felt by psychiatric patients (e.g., pain where no physical cause may exist), and wandering pain (e.g., wherein the pain repeatedly changes location in the body). In certain embodiments, non-inflammatory pain and/or inflammatory pain are associated with disorders such as inflammatory diseases (e.g., autoimmune disease).

In certain embodiments, the FAAH-mediated disorder is an inflammatory disorder. The term "inflammatory disorders" refers to those diseases or conditions that are characterized by signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and/or loss of function (functio laesa, which can be partial or complete, temporary or permanent). Inflammatory disorders include, without limitation, those affecting the blood vessels (e.g., polyarteritis, temporal arteritis); joints (e.g, arthritis: crystalline, osteo-, psoriatic, reactive, rheumatoid, Reiter's syndrome); gastrointestinal tract (e.g, Crohn's disease, ulcerative colitis); skin (e.g, dermatitis); or multiple organs and tissues (e.g, systemic lupus erythematosus). Inflammatory disorders include, but are not limited to, inflammation associated with vascular diseases, migraine headaches, tension headaches, arteritis, thyroiditis, aplastic anemia, Hodgkin's disease, scleroderma, rheumatic fever, type I diabetes, myasthenia gravis, sarcoidosis, nephrotic syndrome, Behcet's syndrome, polymyositis, gingivitis, hypersensitivity, conjunctivitis, multiple sclerosis, and ischemia (e.g., myocardial ischemia), and the like. The compounds and compositions can be useful for treating neuroinflammation associated with brain disorders (e.g., Parkinson's disease and Alzheimer's disease) and chronic inflammation associated with cranial radiation injury. The compounds can be useful for treating acute inflammatory conditions (e.g., conditions resulting from infection) and chronic inflammatory conditions (e.g., conditions resulting from asthma, arthritis and inflammatory bowel disease). The compounds can also be useful in treating inflammation associated with trauma and non-inflammatory myalgia. Inflammation takes on many forms and includes, but is not limited to, acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative inflammation.

In certain embodiments, the FAAH-mediated disorder is an immune disorder. Immune disorders, such as auto-immune disorders, include, but are not limited to, arthritis (including rheumatoid arthritis, spondyloarthopathies, gouty arthritis, degenerative joint diseases such as osteoarthritis, systemic lupus erythematosus, Sjogren's syndrome, ankylosing spondylitis, undifferentiated spondylitis, Behcet's disease, haemolytic autoimmune anaemias, multiple sclerosis, amyotrophic lateral sclerosis, amylosis, acute painful shoulder, psoriatic, and juvenile arthritis), asthma, atherosclerosis, osteoporosis, bronchitis, tendonitis, bursitis, skin inflammation disorders (e.g., psoriasis, eczema, burns, dermatitis), enuresis, eosinophilic disease, gastrointestinal disorders (e.g., inflammatory bowel disease (IBD), peptic ulcers, regional enteritis, diverticulitis, gastrointestinal bleeding, Crohn's disease, gastritis, diarrhoea, irritable bowel syndrome and ulcerative colitis), and disorders ameliorated by a gastroprokinetic agent (e.g., ileus, postoperative ileus and ileus during sepsis; gastroesophageal reflux disease (GORD, or its synonym GERD); eosinophilic esophagitis, gastroparesis such as diabetic gastroparesis; food intolerances and food allergies and other functional bowel disorders, such as non-ulcerative dyspepsia (NUD) and non-cardiac chest pain (NCCP, including costo-chondritis)).

In certain embodiments, the immune disorder is a gastrointestinal disorder. In some embodiments, the immune disorder is inflammatory bowel disease (e.g., Crohn's disease and/or ulcerative colitis), peptic ulcers, regional enteritis, diverticulitis, gastrointestinal bleeding, Crohn's disease, gastritis, diarrhea, irritable bowel syndrome and ulcerative colitis. In other embodiments, the immune disorder is inflammatory bowel disease (IBD).

In certain embodiments, the FAAH-mediated disorder is a skin disorder. In some embodiments, the skin disorder is pruritus (itch), psoriasis, eczema, burns or dermatitis. In certain embodiments, the skin disorder is psoriasis. In certain embodiments, the skin disorder is pruritis.

In certain embodiments, the FAAH-mediated disorder is anxiety. "Anxiety," as used herein, includes, but is not limited to anxiety and anxiety disorders or conditions, such as, for example, clinical anxiety, panic disorder, agoraphobia, generalized anxiety disorder, specific phobia, social phobia, obsessive-compulsive disorder, acute stress disorder, and post-traumatic stress disorder; and adjustment disorders with anxious features, anxiety disorders associated with depression, anxiety disorders due to general medical conditions, and substance-induced anxiety disorders. This treatment can also be to induce or promote sleep in a patient (e.g., for example, a subject with anxiety).

In certain embodiments, the FAAH-mediated disorder is a sleep disorder. "Sleep disorders" include, but are not limited to, insomia, sleep apnea, restless legs syndrome (RLS), delayed sleep phase syndrome (DSPS), periodic limb movement disorder (PLMD), hypopnea syndrome, rapid eye movement behavior disorder (RBD), shift work sleep disorder (SWSD), and sleep problems (e.g., parasomnias) such as nightmares, night terrors, sleep talking, head banging, snoring, and clenched jaw and/or grinding of teeth (bruxism).

In certain embodiments, the FAAH-mediated disorder is depression. "Depression," as used herein, includes, but is not limited to, depressive disorders or conditions, such as, for example, major depressive disorders (unipolar depression), dysthymic disorders (chronic, mild depression) and bipolar disorders (manic-depression). The depression can be clinical or subclinical depression.

In certain embodiments, the FAAH-mediated disorder is feeding behavior. "Feeding behavior," as used herein, includes but is not limited to, eating disorders (e.g., anorexias and cachexias of various natures, over-eating leading to obesity), weight loss associated with cancer, weight loss associated with other general medical conditions, weight loss associated with failure to thrive, and other wasting conditions. The compounds disclosed herein can also be used to reduce body fat and for treating or preventing obesity in a mammal. The compounds disclosed herein can also be used for preventing or treating the diseases associated with these health conditions.

In certain embodiments, the FAAH-mediated disorder is a movement disorder. In other embodiments, the FAAH-mediated disorder is glaucoma. In yet other embodiments, the FAAH-mediated disorder is neuroprotection. In still yet other embodiments, the FAAH-mediated disorder is cardiovascular disease.

Administration

Provided compounds can be administered using any amount and any route of administration effective for treatment. The exact amount required will vary from subject to subject, depending on the species, age, and general condition of the subject, the severity of the infection, the particular composition, its mode of administration, its mode of activity, and the like.

Compounds provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease, disorder, or condition being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including oral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, enteral, sublingual; by intratracheal instillation, bronchial instillation, and/or inhalation; and/or as an oral spray, nasal spray, and/or aerosol. Specifically contemplated routes are systemic intravenous injection, regional administration via blood and/or lymph supply, and/or direct administration to an affected site. In general the most appropriate route of administration will depend upon a variety of factors including the nature of the agent (e.g., its stability in the environment of the gastrointestinal tract), the condition of the subject (e.g., whether the subject is able to tolerate oral administration), etc.

The exact amount of a compound required to achieve a therapeutically effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, a therapeutically effective amount of a compound for administration one or more times a day to a 70 kg adult human can comprise about 0.0001 mg to about 1000 mg of an inventive compound per unit dosage form. For example, a therapeutically effective amount of a compound of the present invention can comprise about 0.01 mg, about 0.5 mg, about 1 mg, about 2, mg, about 3 mg, about 5 mg, about 10 mg, about 25 mg, about 50 mg, about 70 mg, about 100 mg, about 200 mg, about 300 mg, about 400 mg, about 500 mg, about 600 mg, about 700 mg, about 800 mg, about 900 mg, or about 1000 mg depending on the compound, the disease and its severity, and the age, weight, etc., of the subject to be treated. It will be appreciated that dose ranges as described herein provide guidance for the administration of provided pharmaceutically acceptable compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional therapeutically active agents. The compound or composition can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the inventive compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

The compounds or compositions can be administered in combination with agents that improve their bioavailability, reduce and/or modify their metabolism, inhibit their excretion, and/or modify their distribution within the body. It will also be appreciated that therapy employed can achieve a desired effect for the same disorder (for example, a compound can be administered in combination with an anti-inflammatory, anti-anxiety and/or anti-depressive agent, etc.), and/or it can achieve different effects (e.g., control of adverse side-effects).

Exemplary active agents include, but are not limited to, anti-cancer agents, antibiotics, anti-viral agents, anesthetics, anti-coagulants, inhibitors of an enzyme, steroidal agents, steroidal or non-steroidal anti-inflammatory agents, antihistamine, immunosuppressant agents, anti-neoplastic agents, antigens, vaccines, antibodies, decongestants, sedatives, opioids, pain-relieving agents, analgesics, anti-pyretics, hormones, prostaglandins, progestational agents, anti-glaucoma agents, ophthalmic agents, anti-cholinergics, anti-depressants, anti-psychotics, hypnotics, tranquilizers, anti-convulsants, muscle relaxants, anti-spasmodics, muscle contractants, channel blockers, miotic agents, anti-secretory agents, anti-thrombotic agents, anticoagulants, anti-cholinergics, β-adrenergic blocking agents, diuretics, cardiovascular active agents, vasoactive agents, vasodilating agents, anti-hypertensive agents, angiogenic agents, modulators of cell-extracellular matrix interactions (e.g. cell growth inhibitors and anti-adhesion molecules), or inhibitors/intercalators of DNA, RNA, protein-protein interactions, protein-receptor interactions, etc. Active agents include small organic molecules such as drug compounds (e.g., compounds approved by the Food and Drugs Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins and cells.

In certain embodiments, the additional therapeutically active agent is a pain-relieving agent. In other embodiments, the additional therapeutically active agent is an anti-inflammatory agent.

Methods of Determining Biological Activity

Methods of determining the activity of the compounds provided herein for various therapeutic uses are known in the art. These include, but are not limited to, high throughput screening to identify compounds that bind to and/or modulate the activity of isolated FAAH, as well as in vitro and in vivo models of therapies.

Assays useful for screening the compounds provided herein can detect the binding of the inhibitor to FAAH or the release of a reaction product (e.g., fatty acid amide or ethanolamine) produced by the hydrolysis of a substrate such as oleoylethanolamide or ananadamide. The substrate can be labeled to facilitate detection of the released reaction products. U.S. Pat. No. 5,559,410 discloses high throughput screening methods for proteins, and U.S. Pat. Nos. 5,576,220 and 5,541,061 disclose high throughput methods of screening for ligand/antibody binding.

Methods for screening FAAH inhibitors for an antinociceptive effect are known in the art. For example, compounds can tested in the mouse hot-plate test and the mouse formalin test, and the nociceptive reactions to thermal or chemical tissue damage measured (for example, see U.S. Pat. No. 6,326,156 for a description of methods of screening for antinociceptive activity; see also Cravatt et al. *Proc. Natl. Acad. Sci. U.S.A.* (2001) 98:9371-9376).

Two pharmacologically validated animal models of anxiety are the elevated zero maze test, and the isolation-induced ultrasonic emission test. The zero maze consists of an elevated annular platform with two open and two closed quadrants and is based on the conflict between an animal's instinct to explore its environment and its fear of open spaces (see, for example, Bickerdike, M. J. et al., *Eur. J. Pharmacol.*, (994) 271, 403-411; Shepherd, J. K. et al., *Psychopharmacology*, (1994) 116, 56-64). Clinically used anxiolytic drugs, such as the benzodiazepines, increase the proportion of time spent in, and the number of entries made into, the open compartments.

A second test for an anti-anxiety compound is the ultrasonic vocalization emission model, which measures the number of stress-induced vocalizations emitted by rat pups removed from their nest (see, for example, Insel, T. R. et al., Pharmacol. Biochem. Behav., 24, 1263-1267 (1986); Miczek, K. A. et al., Psychopharmacology, 121, 38-56 (1995); Winslow, J. T. et al., Biol. Psychiatry, 15, 745-757 (1991).

The effect of the compounds provided herein in the treatment of depression can be tested in the model of chronic mild stress induced anhedonia in rats. This model is based on the observation that chronic mild stress causes a gradual decrease in sensitivity to rewards, for example consumption of sucrose, and that this decrease is dose-dependently reversed by chronic treatment with antidepressants. See, e.g., Willner, Paul, Psychopharmacology, 1997, 134, 319-329.

Another test for antidepressant activity is the forced swimming test (Nature 266, 730-732, 1977). In this test, animals are administered an agent 30 or 60 minutes before being placed in container of water, and the time during which they remain immobile is recorded. A decrease in the immobility time of the mice is indicative of antidepressant activity.

A similar test for antidepressant activity is the mouse caudal suspension test (Psychopharmacology, 85, 367-370, 1985). In this test, animals are administered an agent 30 or 60 minutes before being suspended by the tail, and their immobility time is recorded. A decrease in the immobility time of the mice is indicative of antidepressant activity.

Animal models are available for assessing anticonvulsant activity of test compounds (see, e.g., U.S. Pat. Nos. 6,309,406 and 6,326,156).

Inhibition of FAAH has been reported to induce sleep in test animals (see, e.g., U.S. Pat. No. 6,096,784). Methods for studying sleep inducing compounds are known in the art (see, e.g., U.S. Pat. Nos. 6,096,784 and 6,271,015). Compounds can be administered to a test animal (e.g., rat or mouse) or a human and the subsequent time (e.g., onset, duration) spent sleeping (e.g., eyes closed, motor quiescence) can be monitored. See also WO 98/24396.

Methods for screening FAAH inhibitors which induce catalepsy are also well known in the art (see, e.g., Quistand et al. in Toxicology and Applied Pharmacology 173: 48-55 (2001); Cravatt et al. Proc. Natl. Acad. Sci. U.S.A. 98:9371-9376 (2001)).

Methods of assessing appetitive behavior are known in the art (see, e.g., U.S. Pat. No. 6,344,474). One method of assessing the effect on appetite behavior is to administer a FAAH inhibitor to a rat and assess its effect on the intake of a sucrose solution (see, e.g., W. C. Lynch et al., Physiol. Behav., 1993, 54, 877-880).

Methods of Synthesis

The reaction of an organometallic species with an organic borate, such as trimethyl borate, can be used to synthesize boronate esters. Suitable organometallic species include, but are not limited to, alkyl lithium and Grignard reagents. Other methods for the synthesis of boronates are employed when the boronate contains sensitive functionality that may not tolerate alkyl lithium reagents or Grignard reagents. These methods include palladium coupling reactions of aryl or akenyl halides and diboronates or dialkoxy boranes and hydroboration of alkenes or alkynes. Using these methods a diverse collection of boronates can be synthesized. Boronates can be readily transformed in to boronic acids by hydrolyzing the boronate under aqueous acidic conditions using a suitable acid. Suitable acids include, but are not limited to HCl, $H_2SO_4$, and HBr. Another method of hydrolyzing boronates is an oxidative hydrolysis employing an oxidizing agent, such as $NaIO_4$. The boronic acid compounds of the present invention readily form boronic esters when exposed to alcohols. The resulting boronic esters can also be used in the methods provided herein. Cyclic boronates are formed when certain diols (e.g., 1,2- and 1,3-diols) are used. Boronic acid compounds provided herein readily form oligomeric anhydrides by dehydration of the boronic acid moiety to form dimers, trimers, and tetramers, and mixtures thereof. These species in the presence of water and under physiological conditions convert back to the boronic acid by hydrolysis.

EXEMPLIFICATION

The invention now being generally described, it will be more readily understood by reference to the following examples, which are included merely for purposes of illustration of certain aspects and embodiments of the present invention, and are not intended to limit the invention.
General Synthetic Methods The following is a description of general synthetic routes that can be used to prepare compounds of the present invention. Additionally, one of skill in the art will recognize that protecting groups may be necessary for the preparation of certain compounds and will be aware of those conditions compatible with a selected protecting group. Examples of such protecting groups include, for example, those set forth in Protective Groups in Organic Synthesis, Greene, T. W.; Wuts, P. G. M., John Wiley & Sons, New York, N.Y., (3rd Edition, 1999). Accordingly, the exemplary methods and the examples described herein are illustrative of the present invention and are not to be construed as limiting the scope thereof.
Method 1:

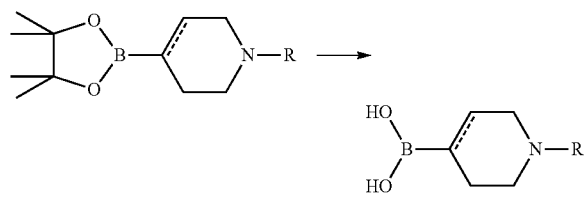

General conditions for the conversion of boronate esters to boronic acids: The boronate ester (1.0 eq), sodium periodate (5.0 eq) and ammonium acetate (5.0 eq) are dissolved in acetone/water 2:1 (0.05 M boronate ester) and stirred for 12 hours at 23° C. until TLC or LCMS indicated conversion to the boronic acid is complete. One option for isolation is to precipitate the product by dilution of the mixture with 1N aqueous HCl and collection of the solid boronic acid by filtration. Alternately, the mixture is partitioned between water and ethyl acetate, and the organic layer washed with brine, dried over sodium sulfate, and concentrated in vacuo. The residue is purified either by recrystallization and trituration (heptane, acetonitrile, or other solvents) or by flash silica gel chromatography (0.5% to 10% methanol/dichloromethane) to afford pure boronic acid.
Method 2:
General conditions for the conversion of boronate esters to boronic acids: The boronate ester (1.0 eq), and sodium periodate (3.0 eq) are dissolved in acetone/water 2:1 (0.05 M boronate ester) after which point 1N HCl (1.5 eq) is added and the reaction is stirred for 12 h at 23° C. until TLC or LCMS indicated conversion to the boronic acid is complete. One option for isolation is to precipitate the product by dilution of the mixture with additional 1N aqueous HCl and collection of the solid boronic acid by filtration. Alternately, the mixture can be partitioned between water and ethyl acetate, and the organic layer washed with brine, dried over sodium sulfate, and concentrated in vacuo. The residue is purified either by recrystallization and trituration (heptane, acetonitrile, or other solvents) or by flash silica gel chromatography (0.5% to 10% methanol/dichloromethane) to afford pure boronic acid.
Method 3:

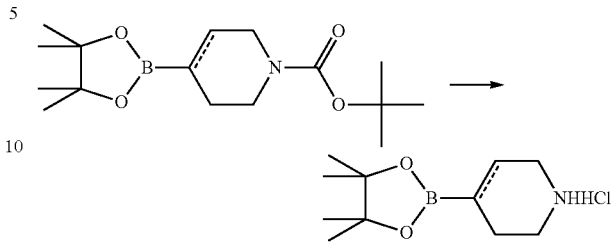

General conditions for the deprotection of a N-Boc carbamate in the presence of a boronate ester: The boronate ester is dissolved in tert-butylmethylether (0.4 M final ester concentration) after which point HCl (g) is bubbled in over the course of 15 min. The reaction is allowed to stir at room temperature for an additional hour after which point the solvent is removed under a stream of nitrogen to provide the desired HCl amine salt as a white solid in quantitative yield.
Method 4:

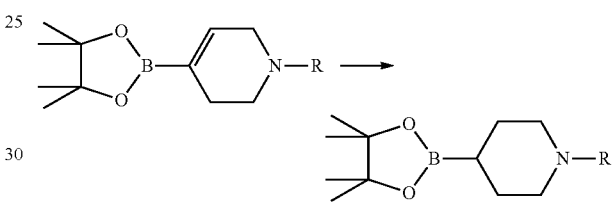

General conditions for the reduction of tetrahydropyridines to piperidines in the presence of a boronate ester: The boronate ester is dissolved in ethyl acetate/methanol (1:1 v/v) (0.4 M final ester concentration) after which $Pd(OH)_2$ (0.35 equiv) is added and the reaction is allowed to stir under an atmosphere of $H_2$ for 14 h. At this point the reaction is filtered through and concentrated in vacuo to provide the desired piperidine in quantitative yield.

EXAMPLES

Exemplary compounds are set forth in the Examples provided below. Compounds were assayed as inhibitors of human FAAH using the method described in detail in Example 19. Activity designated as "A" refers to compounds having a $K_i$ of less than or equal to 0.01 µM, "B" refers to compounds having a $K_i$ of between 0.01 µM and 0.1 µM, "C" refers to compounds having a $K_i$ of between 0.1 µM and 1 µM, and "D" refers to compounds having a $K_i$ of greater than 1 µM.

Example 1

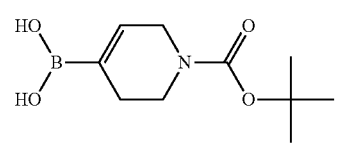

Tetrahydropyridine 1 was prepared in 1 step from commercially available 4-(4,4,5,5-tetramethyl-1,3,2-dioxaborolan-2-yl)-1,2,3,6-tetrahydropyridine-1-carboxylate using Method 1 and was isolated after precipitation from the reaction mixture. [M-H]−=226.1 m/z. Activity: C

Example 2

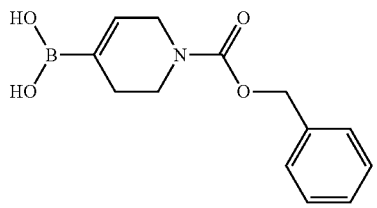

Tetrahydropyridine 2 was prepared in 3 steps starting with the deprotection of 1 using Method 3. The resulting HCl amine salt was dissolved in dichloromethane (0.2 M). Benzyl chloroformate (1.2 equiv) was added followed by triethylamine (3.0 equiv). The reaction was allowed to stir at room temperature for 2 h after which point it was diluted with 1N HCl and extracted with excess dichloromethane. The organic layer was dried over $MgSO_4$ and concentrated to provide the desired carbamate in quantitative yield, which was converted directly to boronic acid 2 using Method 2. [M-H]−=260.1 m/z. Activity: B

Example 3

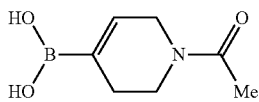

Tetrahydropyridine 3 was prepared as described in Example 2, except that acetyl chloride was used in place of benzyl chloroformate. Activity: D

Example 4

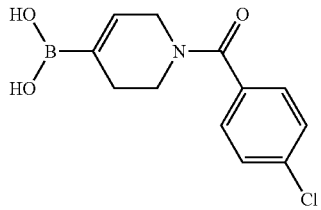

Tetrahydropyridine 4 was prepared as described in Example 2, except that 4-chlorobenzoyl chloride was used in place of benzyl chloroformate. Activity: B

Example 5

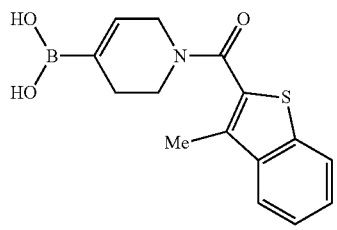

Tetrahydropyridine 5 was prepared in 2 steps starting with the deprotection of 1 using Method 3. The resulting HCl amine salt was dissolved in N,N-dimethylformamide (0.2 M). 3-Methyl-1-benzothiophene-2-carboxylic acid (1.0 equiv) and PyBOP (1.0 equiv) were added followed by the dropwise addition of triethylamine (3.0 equiv). After stirring at room temperature for 30 min, the reaction was diluted with water and filtered. The isolated material was then purified using semi-preparatory liquid chromatography to isolate the fraction of desired boronic acid 5 that resulted from pinacol ester deprotection during the course of the acid coupling. [M-H]−=300.1 m/z. Activity: B

Example 6

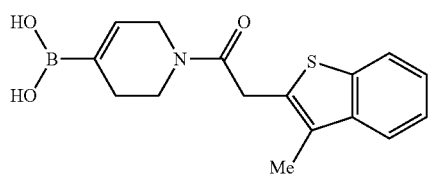

Tetrahydropyridine 6 was prepared as described in Example 5 except that (3-methyl-1-benzothien-2-yl)acetic acid was used in place of 3-methyl-1-benzothiophene-2-carboxylic acid. Activity: B

Example 7

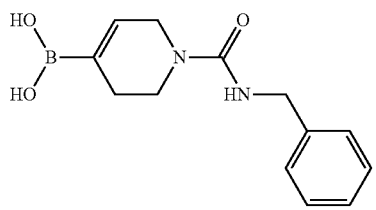

Tetrahydropyridine 7 was prepared in 3 steps starting with the deprotection of 1 using Method 3. The resulting HCl amine salt was suspended in dichloromethane (0.2 M). Triphosgene (0.67 equiv) was added followed by benzylamine (2.67 equiv) and triethylamine (5.0 equiv) after which point the reaction became homogeneous. The reaction was allowed to stir at room temperature for 2 h after which point it was diluted with 1N HCl and extracted with excess dichloromethane. The organic layer was dried over $MgSO_4$, and concentrated to provide the desired urea which was converted directly to boronic acid 7 using Method 2 and isolated using semi-preparatory reverse phase liquid chromatography. [M-H]−=259.1 m/z. Activity: B

Example 8

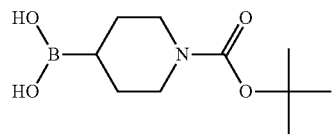

Piperidine 8 was prepared in 2 steps from compound 1 using Method 4 followed by pinacol ester deprotection using Method 2. [M-H]-=228.2 m/z. Activity: B Example 9

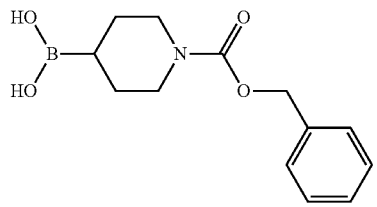

9

Piperidine 9 was prepared in 4 steps from compound 1 using Method 4 followed by Boc deprotection using Method 3. The resulting amine HCl salt was treated with benzyl chloroformate using the same conditions as in Example 2 followed by pinacol ester deprotection using Method 2. [M-H]-=262.1 m/z. Activity: B Example 10

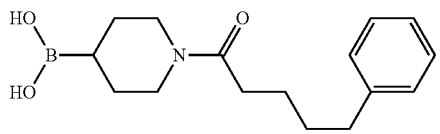

10

Piperidine 10 was prepared in 4 steps from compound 1 using Method 4 followed by Boc deprotection using Method 3. The resulting amine HCl salt was treated with 5-phenyl-propionic acid using the coupling conditions outlined in Example 5 followed by pinacol ester deprotection using Method 2. The product was isolated using semi-preparatory reverse phase liquid chromatography. [M-H]-=288.2 m/z. Activity: B Example 11

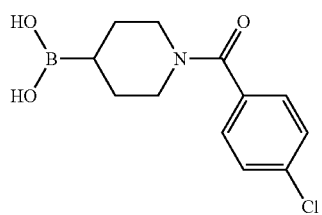

11

Piperidine 11 was prepared in 4 steps from compound 1 using Method 4 followed by Boc deprotection using Method 3. The resulting amine HCl salt was treated with 4-chlorobenzoyl chloride using the coupling conditions outlined in Example 2. The product was isolated using flash silica gel chromatography (gradient of hexanes/ethyl acetate). The desired boronic acid was isolated using semi-preparatory reverse phase liquid chromatography followed by pinacol ester deprotection using Method 2. [M-H]-=266.1 m/z. Activity: C Example 12

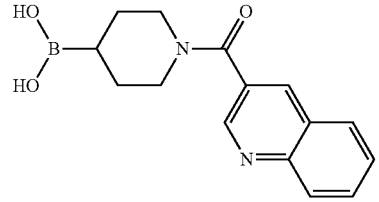

12

Piperidine 12 was prepared in 4 steps from compound 1 using Method 4 followed by Boc deprotection using Method 3. The resulting amine HCl salt was treated with quinoline-3-carboxylic acid using the coupling conditions outlined in Example 5. The desired boronic acid was isolated using semi-preparatory reverse phase liquid chromatography followed by pinacol ester deprotection using Method 2. [M-H]-=288.2 m/z. Activity: C Example 13

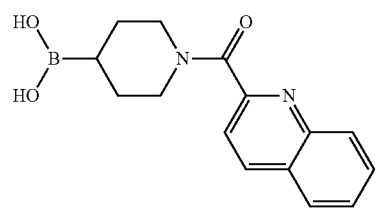

13

Piperidine 13 was prepared in 4 steps from compound 1 using Method 4 followed by Boc deprotection using Method 3. The resulting amine HCl salt was treated with quinaldic acid using the coupling conditions outlined in Example 5. The desired boronic acid was isolated using semi-preparatory reverse phase liquid chromatography followed by pinacol ester deprotection using Method 2. [M-H]-=288.2 m/z. Activity: C Example 14

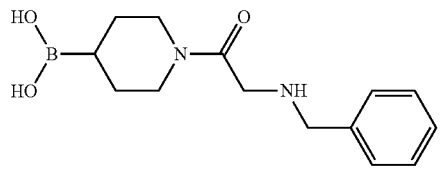

14

Piperidine 14 was prepared in 3 steps from compound 1 using Method 4 followed by Boc deprotection using Method 3. The resulting amine HCl salt was treated with N-benzylglycine using the coupling conditions outlined in Example 5 to provide a mixture of pinacol ester boronate and the desired boronic acid 14 which was isolated using semi-preparatory reverse phase liquid chromatography. [M-H]−=275.2 m/z. Activity: D Example 15

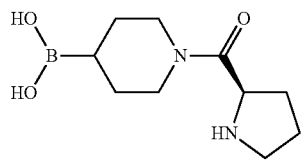

Piperidine 15 was prepared in 3 steps from compound 1 using Method 4 followed by Boc deprotection using Method 3. The resulting amine HCl salt was treated with L-proline using the coupling conditions outlined in Example 5 to provide a mixture of Boc-deprotected pinacol ester boronate and the desired boronic acid 15 which was isolated using semi-preparatory reverse phase liquid chromatography. [M-H]−=225.1 m/z. Activity: D Example 16

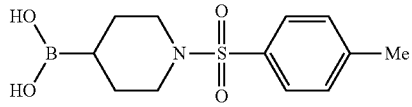

Piperidine 16 was prepared in 4 steps from compound 1 using Method 4 followed by Boc deprotection using Method 3. The resulting amine HCl salt was treated with 4-methylbenzene sulfonyl chloride using the same conditions outlined in Example 2 followed by pinacol ester deprotection using Method 2. [M-H]−=282.1 m/z. Activity: C Example 17

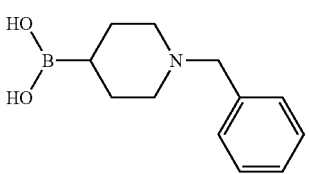

Piperidine 17 was prepared in 4 steps from compound 1 using Method 4 followed by Boc deprotection using Method 3. The resulting amine HCl salt was suspended in methylene chloride (0.2 M) and benzyl bromide (3.0 equiv) was added followed by the addition of triethylamine (1.0 equiv). The reaction was allowed to stir at room temperature for 14 h after which point it was diluted with 1N HCl and extracted with excess diethyl ether/hexane (1:1 v/v). The aqueous layer was then basified with NaHCO₃ and extracted with ethyl acetate. The organic layer was dried over MgSO₄ and concentrated to provide the desired tertiary amine, which was converted directly to boronic acid 17 using Method 2 and isolated using semi-preparatory reverse phase liquid chromatography. [M-H]−=218.1 m/z. Activity: D Example 18

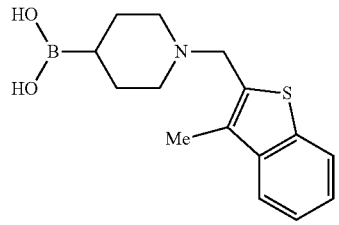

(3-Methyl-1-benzothien-2-yl)methanol was dissolved in methylene chloride (0.2 M). Methane sulfonyl chloride (1.1 equiv) was added followed by triethylamine (1.1 equiv) and the reaction was allowed to stir overnight at room temperature after which point it was diluted with 1N HCl and extracted with excess dichloromethane. The organic layer was dried over MgSO₄, and concentrated to provide the desired mesyl alcohol in quantitative yield. This mesyl alcohol (1.3 equiv) was added to a suspension of 4-(4,4,5,5-tetramethyl-1,3,2-dioxaborolan-2-yl)piperidien hydrochloride (formed from compound 1 using Method 4 followed by Boc deprotection using Method 3) followed by the addition of triethylamine (4.0 equiv). The reaction was allowed to stir overnight at room temperature after which point it was diluted with 1N HCl and extracted with excess dichloromethane. The organic layer was dried over MgSO₄, and concentrated to provide a mixture of pinacol ester boronate and the desired boronic acid 18 which was isolated using semi-preparatory reverse phase liquid chromatography. [M-H]−=288.1 m/z. Activity: B Example 19

Inhibition of Rat and Human FAAH

The following assays can be used to determine the inhibition of FAAH: (1) a fluorescence-based assay (Manjunath et al., *Analytical Biochemistry* (2005) 343:143-151); and (2) a microsome-based fluorescent assay (Wang et al., *Biomolecular Screening* (2006) 1-9).

Rat FAAH Preparation:

Five rat livers were homogenized in five fold volume with ice cold Tris (20 mM pH 8.0) and 0.32 M Sucrose solution via an Ultra Turrax T25 homogenizer. All subsequent preparation steps were carried out at 4° C. The homogenate was centrifuged at 6000 g, for 20 minutes and the pellet, containing nuclear debris and mitochondria was discarded. The supernatant was centrifuged at 40,000 g for 30 minutes. The supernatant was discarded and the pellet solubilized via a dounce homogenizer in resuspension buffer (20 mM Hepes pH 7.8, 10% v/v glycerol, 1 mM EDTA, 1% triton X-100) overnight at 4° C. to resolubilize membrane bound FAAH. The solution was centrifuged at 40,000 g for 30 minutes and the pellet discarded. The supernatant containing rat FAAH was aliquoted and flash frozen with liquid nitrogen and stored for long term usage at −80° C.

Human FAAH Preparation:

COS-7 cells were split the day before, 1:5 into 150 mm×25 mm cell culture dishes (Corning Inc., Cat. No. 430599). Transient transfection took place at 30-40% confluency according to FuGENE 6 Transfection Reagent (Roche, Cat. No. 11814 443 001).

Transfection Procedure:

The FuGENE transfection 6 reagent (45 uL) was added to 1410 µL of media (DMEM, serum free without pen/strep) in a 15 mL conical tube and incubated at room temp for 5 minutes, followed by the addition of FAAH plasmid DNA (15 ng) (OriGene Cat. No. TC119221, Genbank Accession No. NM_001441.1, 0.67 ug/uL) and a further incubation of 15 minutes at room temperature. The resulting solution was added into one dish of 30-40% confluent COS-7 cells in a drop-wise manner. The COS-7 cell dish was subsequently incubated for 48 hours. The cells were then harvested.

Harvest Procedure:

Media was aspirated from the dishes and the cells rinsed with 10 mL PBS. The PBS was removed and 3 mL of PBS added to the dish. The dish was scraped to resuspend the cells, and the subsequent cell suspension collected into a 15 mL conical tube. The cells were pelleted by centrifugation at 1200 rpm for 5 minutes in a bench top centrifuge. PBS was removed and the cell pellet snap frozen in liquid nitrogen and stored at −80° C.

COS-7 Cells—FAAH Purification:

(1) Fractionation: Frozen cell pellets from transient transfections were thawed on ice and resuspended in 12.5 mM Hepes pH 8.0, 100 mM NaCl, 1 mM EDTA (10 mL/0.2 g cell pellet). The pellets were dounce homogenized and then sonicated to produce cell extract. The cell extract was subsequently centrifuged at 1000 g to remove cellular debris. The pellet was discarded and the supernatant centrifuged at 13,000 g for 20 minutes. The pellet contained membrane bound FAAH. The supernatant was discarded and the pellet resolubilized.

(2) Re-solubilization: The fraction of interest, (13,000 g, membrane fraction) was re-suspended in 2.3 mL re-suspension buffer (20 mM Hepes pH 7.8, 10% v/v Glycerol, 1 mM EDTA, 1% Triton X-100) and the sample incubated on ice for 1 hour and then centrifuged to remove any particulate matter. The supernatant containing solubilized human FAAH was aliquoted and snap frozen in liquid nitrogen and stored at −80° C. until use.

(3) Characterization: Protein Concentration determined by Bradford assay.

SDS gel and Western blot to confirm presence of FAAH

FAAH activity assay

Km determination—96-well assay

Linear dependence—96-well assay

Standard compound Ki determination—384-well assay

Rat FAAH Biochemical Inhibition Assay; Materials and Methods:

Rat FAAH biochemical assays were carried out in a 96 well flat bottom black non-treated polystyrene plates (Corning Costar Catalogue #3915). FAAH reaction buffer: 50 mM Hepes (pH 7.5), 1 mM EDTA, 0.2% Triton X-100. FAAH substrate-AMC Arachidonoyl Amide (Cayman Chemicals Company, Catalog #10005098). The reaction was read in an Envision microtiter plate reader [Excitation filter 355 nm (40 nm bandpass); Emission filter 460 nm (25 nm bandpass)]. The raw fluorescence was plotted on the y axis and the inhibitor concentration on the x axis to give a dose response inhibition curve. The data was fitted to a single site competitive inhibition equation, fixing the Km for the rat and human enzyme to 12 µM and 9 µM respectively.

Rat FAAH Biochemical Inhibition Assay; Experimental Protocol:

The principle of this assay was the hydrolysis of AMC-Arichodonoyl, a fluorescent analogue of Anandamide, which results in the formation of Arachidonic acid and AMC. The formation of AMC results in an increase in fluorescence (see, for example, Manjunath et al., *Analytical Biochemistry* (2005) 343:143-151; and Wang et al., *Biomolecular Screening* (2006) 1-9). The inhibition of product formation and hence fluorescence as a function of inhibitor concentration enables the determination of Ki for the compounds.

A 0.49 mg/ml Rat liver FAAH solution was made up in FAAH reaction buffer, and 78 ul pipetted into a 96 well plate. To this was added 2 uL of a 3 fold serially diluted inhibitor from a DMSO stock solution. The FAAH solution and inhibitor were incubated for 30 minutes at room temperature. The FAAH reaction was initiated by the addition of 80 µL of 40 µM AMC Arachidonoyl Amide in FAAH reaction buffer, yielding a final reaction FAAH rat liver preparation concentration of 0.25 mg/mL and AMC-Arachidonoyl substrate concentration of 20 µM, reaction volume 160 µL. The reaction was allowed to proceed for 4 hours at room temperature. The reaction was stopped by the addition of 80 µL 12 uM a-ketoheterocycle (Cayman Chemicals, catalogue #10435). The microtiter plate was read in the envision plate reader.

Human FAAH Assay; Experimental Protocol:

A 0.1 mg/mL Human FAAH solution was made up in FAAH reaction buffer, and 24 ul pipeted into a 384 well plate. To this was added 1 µL of a 3 fold serially diluted inhibitor from a DMSO stock solution. The FAAH solution and inhibitor were incubated for 30 minutes at room temperature. The FAAH reaction was initiated by the addition of 25 µL of 40 µM AMC Arachidonoyl Amide in FAAH reaction buffer, yielding a final reaction human FAAH preparation concentration of 0.05 mg/ml and AMC-Arachidonoyl substrate concentration of 20 µM, reaction volume 50 µL. The reaction was allowed to proceed for 4 hours at room temperature. The reaction was stopped by the addition of 25 µL 12 µM a-ketoheterocycle (Cayman Chemicals, catalogue #10435). The microtiter plate was read in the envision plate reader.

The raw fluorescence was plotted on the y axis and the inhibitor concentration on the x axis to give a dose response inhibition curve. The data was fitted to a single site competitive inhibition equation, fixing the Km for the rat and human enzyme to 12 µM and 9 µM respectively.

The contents of all references, pending patent applications and published patent applications, cited throughout this application are hereby incorporated by reference in their entirety as if each individual publication or patent application were specifically and individually indicated to be incorporated by reference.

Those skilled in the art will recognize, or be able to ascertain using no more than routine experimentation, many equivalents to the specific embodiments of the invention described herein. Such equivalents are intended to be encompassed by the following claims.

We claim:
1. A compound of formula III:

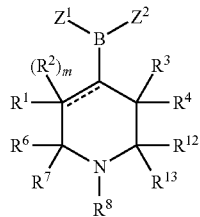

or a pharmaceutically acceptable salt, solvate or prodrug thereof, or mixture thereof, wherein:
----- is selected from a single bond and a double bond;
m is 1 when ----- is a single bond;
m is 0 when ----- is a double bond;
$Z^1$ is —$OR^{14}$;
$Z^2$ is —$OR^{15}$;
$R^1$, $R^2$, $R^3$, $R^4$, $R^6$, $R^7$, $R^{12}$ and $R^{13}$ each independently is selected from H, halogen, $C_{1-6}$ alkyl, $C_{2-6}$ alkenyl, $C_{2-6}$ alkynyl, $C_{1-6}$ perhaloalkyl, —CN, —$OR^{16}$, $NR^{17}R^{18}$, —$C(O)R^{19}$, $C_{3-10}$ carbocyclyl, $C_{6-10}$ aryl, $C_{7-12}$ aralkyl, 3-10 membered cycloheteroalkyl, and 5-10 membered heteroaryl;
$R^8$ is selected from $C_{2-6}$ alkenyl, $C_{2-6}$ alkynyl, —$C(O)R^{20}$, —$C(O)NR^{22}R^{23}$, $S(O)_2R^{24}$, $C_{3-10}$ carbocyclyl, $C_{6-10}$ aryl, 3-10 membered cycloheteroalkyl, 5-10 membered heteroaryl, and —$(CH_2)_p$—$R^{25}$;
$R^{14}$ and $R^{15}$, at each occurrence, each independently is selected from H, $C_{1-6}$ alkyl, $C_{2-6}$ alkenyl, and $C_{2-6}$ alkynyl;
$R^{16}$, at each occurrence, each independently is selected from H, $C_{1-6}$ alkyl, $C_{2-6}$ alkenyl, $C_{2-6}$ alkynyl, $C_{3-10}$ carbocyclyl, $C_{6-10}$ aryl, $C_{7-12}$ aralkyl, 3-10 membered cycloheteroalkyl, and 5-10 membered heteroaryl;
$R^{17}$ and $R^{18}$, at each occurrence, each independently is selected from H, $C_{1-6}$ alkyl, $C_{2-6}$ alkenyl, $C_{2-6}$ alkynyl, —$C(O)R^{26}$, —$C(O)OR^{27}$, $C_{3-10}$ carbocyclyl, $C_{6-10}$ aryl, $C_{7-12}$ aralkyl, 3-10 membered cycloheteroalkyl, and 5-10 membered heteroaryl;
$R^{19}$, at each occurrence, each independently is selected from $C_{1-6}$ alkyl, $C_{2-6}$ alkenyl, $C_{2-6}$ alkynyl, $C_{3-10}$ carbocyclyl, $C_{6-10}$ aryl, $C_{7-12}$ aralkyl, 3-10 membered cycloheteroalkyl, and 5-10 membered heteroaryl;
$R^{20}$ is selected from $C_{1-6}$ alkyl, $C_{2-6}$ alkenyl, $C_{2-6}$ alkynyl, $C_{3-10}$ carbocyclyl, $C_{6-10}$ aryl, 3-10 membered cycloheteroalkyl, 5-10 membered heteroaryl, and —$(CH_2)_q$—$R^{28}$;
$R^{22}$ and $R^{23}$ each independently is selected from H, $C_{1-6}$ alkyl, $C_{2-6}$ alkenyl, $C_{2-6}$ alkynyl, $C_{3-10}$ carbocyclyl, $C_{6-10}$ aryl, 3-10 membered cycloheteroalkyl, 5-10 membered heteroaryl, and —$(CH_2)_r$—$R^{29}$;
$R^{24}$ is selected from $C_{1-6}$ alkyl, $C_{2-6}$ alkenyl, alkynyl, $C_{3-10}$ carbocyclyl, $C_{6-10}$ aryl, 3-10 membered cycloheteroalkyl, 5-10 membered heteroaryl, and —$(CH_2)_t$—$R^{30}$;
$R^{25}$ is selected from $C_{3-10}$ carbocyclyl, $C_{6-10}$ aryl, 3-10 membered cycloheteroalkyl, and 5-10 membered heteroaryl;
$R^{26}$ and $R^{27}$ each independently is selected from $C_{1-6}$ alkyl, $C_{2-6}$ alkenyl, $C_{2-6}$ alkynyl, $C_{3-10}$ carbocyclyl, $C_{6-10}$ aryl, $C_{7-12}$ aralkyl, 3-10 membered cycloheteroalkyl, and 5-10 membered heteroaryl;

$R^{28}$, $R^{29}$, and $R^{30}$, at each occurrence, each independently is selected from —$OR^{31}$, —$NR^{32}R^{33}$, $C_{3-10}$ carbocyclyl, $C_{6-10}$ aryl, 3-10 membered cycloheteroalkyl, and 5-10 membered heteroaryl;
$R^{31}$, $R^{32}$ and $R^{33}$, at each occurrence, each independently is selected from H, $C_{1-6}$ alkyl, $C_{2-6}$ alkenyl, $C_{2-6}$ alkynyl, $C_{3-10}$ carbocyclyl, $C_{6-10}$ aryl, $C_{7-12}$ aralkyl, 3-10 membered cycloheteroalkyl, and 5-10 membered heteroaryl; and
p, q, r, and t, at each occurrence, each independently is selected from 1, 2, 3, 4, 5 and 6.

2. The compound of claim 1, wherein $R^8$ is selected from —$C(O)R^{20}$, —$C(O)NR^{22}R^{23}$, $S(O)_2R_{24}$, and —$(CH_2)_p$—$R^{25}$.

3. The compound of claim 1, wherein $R^8$ is —$C(O)R^{20}$, and $R^{20}$ is selected from $C_{1-6}$ alkyl, $C_{3-10}$ carbocyclyl, $C_{6-10}$ aryl, 3-10 membered cycloheteroalkyl, 5-10 membered heteroaryl, and —$(CH_2)_q$—$R^{28}$.

4. The compound of claim 3, wherein $R^{20}$ is —$(CH_2)_q$—$R^{28}$, and $R^{28}$ is selected from $C_{3-10}$ carbocyclyl, $C_{6-10}$ aryl, 3-10 membered cycloheteroalkyl, and 5-10 membered heteroaryl.

5. The compound of claim 3, wherein $R^{20}$ is —$(CH_2)_q$—$R^{28}$, and $R^{28}$ is —$NR^{32}R^{33}$.

6. The compound of claim 5, wherein $R^{32}$ and $R^{13}$ each independently is selected from H, $C_{1-6}$ alkyl, and $C_{7-12}$ aralkyl.

7. The compound of claim 1, wherein $R^8$ is —$C(O)NR^{22}R^{23}$.

8. The compound of claim 7, wherein $R^{22}$ and $R^{23}$ each independently is selected from H, $C_{1-6}$ alkyl, and —$(CH_2)_r$—$R^{29}$.

9. The compound of claim 8 wherein $R^{29}$ is selected from $C_{6-10}$ aryl and 5-10 membered heteroaryl.

10. The compound of claim 1, wherein $R^8$ is —$S(O)_2R^{24}$.

11. The compound of claim 10, wherein $R^{24}$ is selected from $C_{1-6}$ alkyl, $C_{6-10}$ aryl, 5-10 membered heteroaryl, and —$(CH_2)_t$—$R^{30}$.

12. The compound of claim 1, wherein $R^8$ is —$(CH_2)_p$—$R^{25}$.

13. The compound of claim 12, wherein $R^{25}$ is selected from $C_{6-10}$ aryl and 5-10 membered heteroaryl.

14. The compound of claim 1, wherein $R^{12}$ is H and $R^{13}$ is H.

15. The compound of claim 1, wherein $R^6$ is H and $R^7$ is H.

16. The compound of claim 1, wherein ----- is a double bond and m is 0.

17. The compound of claim 1, wherein ----- is a single bond and m is 1.

18. The compound of claim 17, wherein $R^2$ is H.

19. The compound of claim 1, wherein $R^1$ is H.

20. The compound of claim 1, wherein $R^3$ is H and $R^4$ is H.

21. The compound of claim 1, wherein $R^{14}$ is H and $R^{15}$ is H.

22. The compound of claim 1, wherein the compound is selected from:

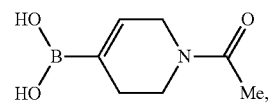

-continued

-continued

, and

or a pharmaceutically acceptable salt, solvate or prodrug thereof, or mixture thereof.

23. A pharmaceutical composition comprising a compound of claim 1 or a pharmaceutically acceptable salt, solvate or prodrug thereof, or mixture thereof and a pharmaceutically acceptable excipient.

24. The compound of claim 1, wherein the compound is of the formula IIIa:

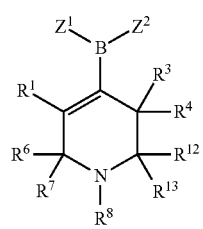

IIIa or a pharmaceutically acceptable salt, solvate or prodrug thereof, or mixture thereof.

25. The compound of claim 1, wherein the compound is of the formula IIIb:

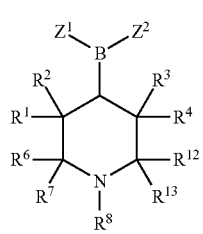

IIIb or a pharmaceutically acceptable salt, solvate or prodrug thereof, or mixture thereof.

* * * * *